US006764683B1

(12) United States Patent
Twardzik et al.

(10) Patent No.: US 6,764,683 B1
(45) Date of Patent: \*Jul. 20, 2004

(54) LOOP PEPTIDE AND TGFα FOR STIMULATING STEM CELL PROLIFERATION AND MIGRATION

(75) Inventors: Daniel R. Twardzik, Bainbridge Island, WA (US); Stefan Paskell, Bainbridge Island, WA (US); Thomas S. Felker, Vashon, WA (US)

(73) Assignee: Kaleidos Pharma, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/459,813

(22) Filed: Dec. 13, 1999

Related U.S. Application Data

(63) Continuation-in-part of application No. 09/299,473, filed on Apr. 26, 1999.

(51) Int. Cl.[7] .................... A61K 38/19; A61K 38/16; A61K 38/12
(52) U.S. Cl. .................... 424/198.1; 514/15; 514/2; 530/324; 530/327; 530/300; 530/317; 530/402; 424/8.5; 930/120
(58) Field of Search .................... 514/2, 11, 12, 514/13, 14, 15; 530/324, 327, 333, 334, 402, 300, 317; 424/85.1, 198.1; 604/19; 930/120

(56) References Cited

U.S. PATENT DOCUMENTS

| | | | |
|---|---|---|---|
| 4,742,003 A | | 5/1988 | Derynck et al. |
| 4,749,683 A | | 6/1988 | Murphy et al. |
| 4,816,561 A | | 3/1989 | Todaro |
| 4,863,899 A | * | 9/1989 | Todaro .................... 514/9 |
| 4,863,902 A | | 9/1989 | Amagase et al. |
| 4,874,746 A | | 10/1989 | Antoniades et al. |
| 5,102,870 A | | 4/1992 | Florine et al. |
| 5,229,493 A | | 7/1993 | Folkman et al. |
| 5,240,912 A | | 8/1993 | Todaro |
| 5,328,986 A | | 7/1994 | Folkman et al. |
| 5,633,147 A | | 5/1997 | Meissner et al. |
| 5,750,376 A | | 5/1998 | Weiss et al. |
| 5,814,308 A | | 9/1998 | Zhang |
| 5,851,832 A | | 12/1998 | Weiss et al. |
| 5,885,956 A | | 3/1999 | Nardi et al. |
| 5,886,141 A | | 3/1999 | Folkman et al. |
| 5,902,799 A | | 5/1999 | Herrmann et al. |
| 5,980,885 A | | 11/1999 | Weiss et al. |
| 5,981,165 A | | 11/1999 | Weiss et al. |
| 6,011,004 A | | 1/2000 | Kessler et al. |
| 6,013,762 A | | 1/2000 | Folkman et al. |
| 6,071,889 A | | 6/2000 | Weiss et al. |
| 6,114,307 A | | 9/2000 | Jaspers et al. |
| 6,232,288 B1 | | 5/2001 | Kojima |
| 6,288,301 B1 | | 9/2001 | Nardi et al. |
| 6,326,201 B1 | | 12/2001 | Fung et al. |

FOREIGN PATENT DOCUMENTS

| | | | |
|---|---|---|---|
| CA | WO9621676 | * | 7/1996 |
| EP | 0 154 434 A1 | | 9/1985 |
| WO | WO 84/01106 | | 3/1984 |
| WO | WO 91/01141 | | 2/1991 |
| WO | WO 94/16718 | | 8/1994 |
| WO | WO 97/25349 | | 7/1997 |
| WO | WO 98/22127 | | 5/1998 |
| WO | WO 98/24468 | | 6/1998 |
| WO | WO 99/06060 | | 2/1999 |
| WO | WO 00/44400 | | 8/2000 |

OTHER PUBLICATIONS

Goodlad, R. A. et al. (1995) "Epidermal growth factor and transforming growth factor–alpha actions on the gut". Euro. J. Gastroentrol. Hepatol. vol. 7, 928–932.*

Doerks, T. et al. (1998) "Protein annotation: detective work for function prediction". TIG vol. 14, p. 248–250.*

Ngo, J. T. et al. et al. (1994) "Computational complexity protein structure prediction, and the levinthal paradox". in "The protein folding problem and tertiary structure prediction". p. 491–495, Merz, Jr. K. et al. Eds. Birkhauser, Boston.*

Nestor et al., "A Synthetic Fragment of Rat Transforming Growth Factor α With Receptor Binding and Antigenic Properties," *Biochemical and Biophysical Research Communications* 129(1):226–232.

Chalazonitis et al., "Transforming Growth Factor α, but Not Epidermal Growth Factor, Promotes the Survival of Sensory Neurons in vitro," *The Journal of Neuroscience* 12(2):583–594 (1992).

Coffey et al., "Transforming Growth Factors and Related Peptides in Gastrointestinal Neoplasia," *Journal of Cellular Biochemistry*, Supp. 16G:111–118 (1992).

Connor and Dragunow, "The role of neuronal growth factors in neurodegenerative disorders of the human brain," *Brain Research Reviews* 27:1–39 (1998).

Draoui et al., "TGFα–PE40 Inhibits Non–Small Cell Lung Cancer Growth," *Life Sciences* 54(7):445–453 (1994).

(List continued on next page.)

*Primary Examiner*—Karen Cochrane Carlson
*Assistant Examiner*—Samuel Wei Liu
(74) *Attorney, Agent, or Firm*—Gray Cary Ware & Freidenrich, LLP; Lisa A. Haile; Kelly K. Reynolds

(57) ABSTRACT

There is disclosed a novel genus of small peptides, much smaller than human TGFα, was discovered as having TGFα biological activity and therefore are useful as pharmacologic agents for the same indications as full length TGFα polypeptide. There is further disclosed that TGFα and consequently the genus of small peptides disclosed herein, was found to have therapeutic activity to stimulate hematopoiesis in patients undergoing cytotoxic cancer chemotherapy and to act as a cytoprotective agent to protect a patient undergoing cancer cytotoxic therapy from gastrointestinal (GI) side effects, such as mucositis and otherwise support the barrier function of the GI tract when it is harmed by cytotoxic therapy.

5 Claims, 10 Drawing Sheets

OTHER PUBLICATIONS

Ferrer et al., "Transforming Growth Factor–α (TGF–α) and Epidermal Growth Factor–Receptor (EGF–R) Immunoreactivity in Normal and Pathologic Brain," *Progress in Neurobiology* 49:99–123 (1996).

Jackson et al., "Effects of Transforming Growth Factor β and Interleukin–1β on Expression of Cyclooxygenase 1 and 2 and Phospholipase $A_2$ mRNA in Lung Fibroblasts and Endothelial Cells in Culture," *Biochemical and Biophysical Rsearch Communications* 97(3):1465–1474 (1993).

Jones et al., "Gastrointestinal Mucosal Regeneration: Role of Growth Factors," *Frontiers in Bioscience* 4:d303–309 (1999).

Liu et al., "TGF–α Can Act as Morphogen and/or Mitogen In a Colon–Cancer Cell Line," *Int. J. Cancer* 56:603–608 (1994).

Liu et al., "Immunohistochemical Study of Transforming Growth Factor–Alpha in Human Lung Cancers," *Tumor Biol.* 13:294–298 (1992).

P. Miettinen, "Transforming Growth Factor–α and Epidermal Growth Factor Expression in Human Fetal Gastrointestinal Tract," *Pediatric Research* 33(5):481–486 (1993).

Mogi et al., "Interleukin–1β, interleukin–6, epidermal growth factor and transforming growth factor–α are elevated in the brain from parkinsonian patients," *Neuroscience Letters* 180:147–150 (1994).

Scheiman et al., "Transforming Growth Factor–Alpha (TGF–α) Levels in Human Proximal Gastrointestinal Epithelium," *Digestive Diseases and Sciences* 42(2):333–341 (1997).

Sottili et al., "Up–regulation of Transforming Growth Factor α Binding Sites in Experimental Rabbit Colitis," *Gastroenterology* 109:24–33 (1995).

Zhang et al., "Transforming growth factor α and a PC–12–derived growth factor induce neurites in PC12 cells and enhance the survival of embryonic brain neurons," *Cell Regulation* 1:511–521 (1990).

Brand, Stephan A. et al., "Prolonged Efficacy of Islet Neogenesis Therapy with Gastrin and TGFα In Mature Rats with Preexisting Diabetes," *Diabetes,* vol. 50 (Supplement), 2001, p. A338.5630.

Burgel, Pierre–Regis et al., "Human Eosinophils Induce Mucin Production In Airway Epithelial Cells Via Epidermal Growth Factor Receptor Activation," *The Journal of Immunology,* 2001, pp. 5948–5954.

Carpenter, Graham et al., "Antibodies to the Epidermal Growth Factor Recptor Block the Biological Activities of Sarcoma Growth Factor," *Proc. Natl. Acad. Sci. USA,* vol. 80, Sep. 1983, pp. 5627–.

Chamberlin, Stephen G. et al., "Constrained Peptide Analogues of Transforming Growth Factor–α Residues Cysteine 21–32 Are Mitogenically Active," *The Journal of Biological Chemistry,* vol. 270, No. 36, Sep. 8, 1995, pp. 21062–21067.

Chosidow, O. et al., "Tripe Palms Associated With Systemic Mastocytosis: The Role of Transforming Growth Factor–α and Efficacy of Interferon–Alfa," *British Journal of Dermatology,* vol. 138, 1998, pp. 698–703.

Chou and Fasman, "Prediction of Protein Conformation," *Biochemistry,* vol. 13, No. 2, 1974, pp. 222–245.

Coffey, Robert J. et al., "Transforming Growth Factors and Related Peptides in Gastrointestinal Neoplasia," *Journal of Cellular Biochemistry,* Supplement 16G, 1992, pp. 111–118.

Dayhoff, M.O. et al., "A Model of Evolutionary Change in Proteins," *Atlas of Protein Sequence and Structure,* 1972, pp. 89–99.

De Larco, Joseph E. et al., "Sarcoma Growth Factor from Mouse Sarcoma Virus–Transformed Cells," *The Journal of Biological Chemistry,* vol. 255, No. 8, Apr. 25, 1980, pp. 3685–3690.

Draoui, Muriel et al., "TGFα–PE40 Inhibits Non–Small Cell Lung Cancer Growth," *Life Sciences,* vol. 54, No. 7, 1994, pp. 445–453.

Dunbar and Goddard, "Structure–function and Biological Role of Betacellulin," *The International Journal of Biochemistry & Cell Biology,* vol. 32, 2000, pp. 805–815.

Ebadi, M. et al., "Neurotrophins and Their Receptors In Nerve Injury and Repair," *Neurochem. Int.,* vol. 30, Nos. 4/5, 1997, pp. 347–374.

Egger, B. "Reduced Susceptibility of Mice Overexpressing Transforming Growth Factor α To Dextran Sodium Sulphate Induced Colitis," *Gut,* vol. 43, 1998, pp. 64–70.

Faber–Elman, A. et al., "Involvement of Wound–Associated Factors In Rat Brain Astrocyte Migratory Response to Axonal Injury In Vitro Simulation," *J. Clin. Invest.,* vol. 97, No. 1, Jan. 1996, pp. 162–171.

Ferrar, Isidre et al., "Transforming Growth Factor–α (TGF–α) and Epidermal Growth Factor–Receptor (EGF–R) Immunoreactivity In Normal and Pathologic Brain," *Progress In Neurobiology,* vol. 49, 1996, pp. 99–123.

Ghielli, Manuela et al., "Regeneration Processes In the Kidney After Acute Injury: Role of Infiltrating Cells," *Exp. Nephrol.,* vol. 6, 1998, pp. 502–507.

Hardie, William D. et al., "Dose–Dependent Lung Remodeling In Transgenic Mice Expressing Transforming Growth factor–α," *Am. J. Physiol. Lung Cell. Mol. Physiol.,* vol. 281, 2001, pp. L1088–L1094.

Hardie, William D. et al., "Attenuation of Acute Lung Injury In Transgenic Mice Expressing Human Transforming Growth factor–α," *Am. J. Physiol.,* vol. 277, 1999, pp. L1045–L1050.

Heidenkummer and Kampik, "Immunohistochemical Localization of Epidermal Growth Factor Receptor In A Human Epiretinal Membrane," *Graefe's Arch. Chn. Exp. Ophthalmol.,* vol. 229, 1991, pp. 492–496.

Ibbotson, K.J. et al., "Tumor–Derived Growth Factor Increases Bone Resorption in A Tumor Associated with Humoral Hypercalcemia of Maignancy," *Science,* vol. 221, pp. 1292–1294.

Jackowski, Andre, "Neural Injury Repair: Hope For the Future As Barriers to Effective CNS Regeneration Become Clearer," *British Journal of Neurosurgery,* vol. 9, 1995, pp. 303–317.

Jackson, Bruce A. et al., "Effects of transforming Growth Factor β and Interleukin–1β on Expression of Cyclooxygenase 1 and 2 and Phospholipase $A_2$ mRNA In Lung Fibroblasts and Endothelial Cells in Culture," *Biochemical and Biophysical Research Communications,* vol. 197, No. 3, Dec. 30, 1993, pp. 1465–1474.

Jayaraman, Gurunathan et al., "Conformational Studies of a Synthetic Cyclic Decapeptide Fragment of Rat Transforming Growth Factor–α," *Int. J. Peptide Protein Res.,* vol. 46, 1995, pp. 88–96.

Jones, M.K. et al., "Gastrointestinal Mucosal Regeneration: Role of Growth Factors," *Frontiers in Bioscience,* vol. 4, Mar. 15, 1999, pp. d303–309.

Kheradmand, Farrah et al., "Transforming Growth Factor–α Enhances Alveolar Epithelial cell Repair In a New In Vitro Model," *Am. J. Physiol.*, vol. 267, 1994, pp. L728–L738.

Kobayashi, Kenzo et al., "The Mechanisms of Gastrointestinal Mucosal Injury and Repair," *Japanese Journal of Clinica*, vol. 56, No. 9, Sep. 15, 1998, pp. 7 (2215)–14 (2222) (English absract).

Konturek, Peter Ch. Et al., "Epidermal Growth Factor and Transforming Growth Factor–α: Role In Protection and Healing of Gastric Mucosal Lesions," *European Journal of Gastroenterology & Hepatology*, vol. 7, 1995, pp. 933–938.

Konturek, S.J. et al., "Transforming Growth Factor Alpha and Epidermal Growth Factor In Protection and Healing of Gastric Mucosal Injury," *Scand. J. Gastroenterol.*, vol. 27, 1992, pp. 649–655.

Kornblum, Harley I. et al., "Prenatal Ontogeny of the Epidermal Growth Factor Receptor and Its Ligand, Transforming Growth Factor Alpha, in the Rat Brain," *The Journal of Comparative Neurology*, vol. 380, 1997, pp. 243–261.

Kudlow, Jeffrey E. et al., "Inability of Anti–Epidermal Growth Factor Receptor Monoclonal Antibody to Block "Autocrine" Growth Stimulation in Transforming Growth Factor–Secreting Melanoma Cells," *The Journal of Biological Chemistry*, vol. 259, No. 19, Oct. 10, 1984, pp. 11895–11900.

Lefebvre, Ph. P. et al., "Regeneration of the Neurosensory Structures in the Mammalian Inner Ear," *Acta. Oto–rhino–laryngologica belg.*, vol. 51, 1997, pp. 1–10.

Leong, Hoyee et al., "Cytostatic Effects of 3,3'–Diindolylmethane In Human Endometrial Cancer Cells Result from an Estrogen Receptor–Mediated Increase in Transforming Growth Factor–α Expression," *Carcinogenesis*, vol. 22, No. 11, 2001, pp. 1809–1817.

Liu, Dan et al., "TGF–α Can Act as Morphogen and/or Mitogen in a Colon–Cancer Cell Line," *Int. J. Cancer*, vol. 56, 1994, pp. 603–608.

Liu, Mark C. et al., "Allergy, Rhinitis, other Respiratory Diseases: Effects of Prednisone On the Cellular Responses and Release of Cytokines and Mediators After Segmental Allergen Challenge of Asthmatic Subjects," *Journal of Allergy and Clinical Immunology*, vol. 108, No. 1, Jul. 2001, 16 pages.

Liu, Ming et al., "Immunohistochemical Study of Transforming Growth Factor–Alpha in Human Lung Cancers," *Tumor Biol.*, vol. 13, 1992, pp. 294–298.

Lord, Bl. Et al., "Kinetics of Neutrophil Production in Normal and Neutropenic Animals During the Response to Filgrastim (r–metHu G–CSF) Filgrastim SD/01 (PEG–r–metHu G–CSF)," *Clin. Cancer Res.*, vol. 7 Jul. 2001, pp. 2085–2090.

Marquardt and Todaro, "Purification and Primary Structure of a Polypeptide with Multiplication–Stimulating Activity from Rat Liver Cell Cultures," *The Journal of Biological Chemistry*, vol. 256, No. 13, Jul. 10, 1981, pp. 6859–6865.

Marquardt, Hans et al., "Transforming Growth Factors Produced By Retrovirus–Transformed Rodent Fibroblasts and Human Melanoma Cells: Amino Acid Sequence Homology with Epidermal Growth Factor," *Proc. Natl. Acad. Sci. USA*, vol. 80, Aug. 1983, pp. 4684–4688.

Miettinen, Paivi J., "Transforming Growth Factor–α and Epidermal Growth Factor Expression in Human Fetal Gastrointestinal Tract," *Pediatric Research*, vol. 33, No. 5, 1993, pp. 481–486.

Mogi, Makio et al., "Interleukin–1β, Interleukin–6, Epidermal Growth Factor and Transforming Growth Factor–α are Elevated in the Brain from Parkinsonian Patients," *Neuroscience Letters*, vol. 180, 1994, pp. 147–150.

Nestor, Jr., John J. et al., "A Synthetic Fragment of Rat Transforming Growth Factor α with receptor Binding and Antigenic Properties," *Biochemical and Biophysical Research Communications*, vol. 129, No. 1, May 31, 1985, pp. 226–232.

Ozanne, Brad et al., "Kirsten Murine Sarcoma Virus transformed Cell Lines and a Spontaneously Transformed rat Cell–Line Produce Transforming Factors," *Journal of Cellular Physiology*, vol. 105, 1980, pp. 163–180.

Reid, S. et al., "Radial Migration of Subependymal Cells in the Adult Rodent Forebrain," *Society for Neuroscience*, vol. 22, 1996, p. 1956 (Abstract).

Rimaniol, Anne–Cecile et al., "Biphasic Transforming Growth Factor–β Production Flanking the Pro–Inflammatory Cytokine Response in Cerebral Trauma," *NeuroReport*, vol. 7, 1995, pp. 133–136.

Romano, Marco et al., "Transforming Growth Factor α Protection Against Drug–Induced Injury to the Rat Gastric Mucosa In Vivo," *J. Clin. Invest.*, vol. 90, 1992, pp. 2409–2421.

Rudinger, J., "Characteristics of the Amino Acids as Componenets of a Peptide Hormone Sequence," *Biological Council: Peptide Hormones*, Jun. 1976, pp. 1–7.

Sagar, S.M. et al., "Rapid Communication: Epidermal Growth Factor and Transforming Growth Factor α Induce c–fos Gene Expression in Retinal Muller Cells In Vivo," *Journal of Neuroscience Research*, vol. 29, 1991, pp. 549–559.

Sasada, Reiko et al., "Cloning and Expression of cDNA Encoding Human Betacellulin, A New Member of the EGF Family," *Biochemical and Biophysical Research Communications*, vol. 190, No. 3, 1993, pp. 1173–1179.

Scheiman, James M. et al., "Transforming Growth Factor–Alpha (TGF–α) Levels in Human Proximal Gastrointestinal Epithelium: Effects of Mucosal Injury and Acid Inhibition," *Digestive Diseases and Sciences*, vol. 42, No. 2, Feb. 1997, pp. 333–341.

Schultz and Twardzik, "Assessment of Biological Activity of Synthetic Fragments of transforming Growth Factor α," *Methods In Enzymology*, vol. 198, 1991, pp. 200–213.

Shing, Y. et al., "Betacellulin: A Mitogen from Pancreatic β Cell Tumors," *Science*, vol. 259, Mar. 12, 1993, pp. 1604–1607.

Skolnick and Fetrow, "From Genes to protein Structure and Function: Novel Applications of Computational Approaches in the Genomic Era," *TIBTECH*, vol. 18, Jan. 2000, pp. 34–38.

Song, Si young et al., "Expansion of Pdx1–Expressing Pancreatic Epithelium and Islet Neogenesis in Transgenic Mice Overexpressing Transforming Growth Factor α," *Gastroenterology*, vol. 117, 1999, pp. 1416–1426.

Sottili, Mauro et al., "Up–Regulation of Transforming Growth Factor α Binding Sites in Experimental Rabbit Colitis," *Gastroenterology*, vol. 109, pp. 24–31.

Sporn and Todaro, "Autocrine Secretion and Malignant Transformation of Cells," *The New England Journal of Medicine*, vol. 303, No. 15, Oct. 9, 1980, pp. 878–880.

Subauste and Proud, "Effects of Tumor Necrosis Factor–α, Epidermal Growth Factor and Transforming Growth Factor–α on Interleukin–8 Production By, and Human Rhinovirus Replication in, Bronchial Epithelial Cells," *International Immunopharmacology,* vol. 1, 2001, pp. 1229–1234.

Todaro, George J. et al., "Transforming Growth Factors (TGFs): Properties and Possible Mechanisms of Action," *Journal of Supramolecular Structure and Cellular Biochemistry,* vol. 15, 1981, pp. 287–301.

Twardzik, Danieal R. et al., "Similar Transforming Growth Factors (TGFs) Produced by Cells Transformed by Different Isolates of Feline Sarcoma Virus," *Virology,* vol. 124, 1983, pp. 201–207.

Weickert and Blum, "Striatal TGF–α: Postnatal Developmental Expression and Evidence for a Role in the Proliferation of Subependymal Cells," *Developmental Brain Research,* vol. 86, 1995, pp. 203–216.

Yamamoto, Koji et al., "Recombinant Human Betacellulin Promotes the Neogenesis of β–Cells and Ameliorates Glucose Intolerance in Mice With Diabetes Induced by Selective Alloxan Perfusion," *Diabetes,* vol. 49, Dec. 2000, pp. 2021–2027.

Yang, Xiao–Dong et al., "Development of ABX–EGF, A Fully Human Anti–EGF Receptor Monoclonal Antibody, for Cancer Therapy," *Critical Reviews in Oncology/Hematology,* vol. 38, 2001, pp. 17–23.

Zhang, Maobin et al., "Transforming Growth Factor α and a PC 12–Derived Growth Factor Induce Neurites in PC12 Cells and Enhance the Survival of Embryonic Brain Neurons," *Cell Regulation,* vol. 1, Jun. 1990, pp. 511–521.

* cited by examiner

TGFα

LOOP PEPTIDE AND TGFα FOR STIMULATING STEM CELL PROLIFERATION AND MIGRATION

This is a continuation-in-part of Ser. No. 09/299,473 filed Apr. 26, 1999.

TECHNICAL FIELD OF THE INVENTION

The present invention provides a novel peptide that is derived from a loop or "lollipop" region of transforming growth factor alpha (TGF-α) and is biologically active for causing stem cells to proliferate and migrate. The present invention further provides a method for augmenting hematopoiesis, particularly trilineage hematopoiesis, and a method for suppressing immune functioning associated with autoimmune diseases, and a method for suppressing inflammatory responses mediated (in part) by excessive histamine release, comprising administering an effective amount of a TGF-α polypeptide or a fragment thereof, such as the lollipop region. The present invention further provides a method for treating or preventing mucositis and gastrointestinal side effects in patients undergoing cancer treatment, comprising administering an effective amount of a TGF-α polypeptide or a fragment thereof, such as the lollipop region.

BACKGROUND OF THE INVENTION

There are several disease treatments that could significantly benefit by having cells regenerate after injury or lesion formation, particularly in the Central Nervous System (CNS), in the immune system and in the gastrointestinal tract. The expression of growth factors and their receptors on the preimplanted human embryo and maternal reproductive tract indicates that such factors influence growth and differentiation of embryonic cells in an autocrine and paracrine manner. Such growth factors are peptides that variously support survival, proliferation, differentiation, size and function of nerve cells and other lineages of ells. EGF (epidermal growth factor) is the first member found of the EGF family and characterized many years ago (Savage and Cohen, *J. Biol. Chem.* 247:7609–7611, 1972; and Savage et al.; *J. Biol. Chem.* 247:7612–7621, 1972). Additional members of the EGF family have been found and they include vaccina virus growth factor (VGF; Ventatesan et al., *J. Virol.* 44:637–646, 1982); myxomavirus growth factor (MGF; Upton et al. *J Virol.* 61:1271–1275, 1987), Shope fibroma virus growth factor (SFGF; Chang et al., *Mol. Cell. Biol.* 7:535–540, 1987), amphiregulin (AR; Kimura et al., *Nature* 348:257–260, 1990), and heparin binding EGF-like factor (HB-EGF; Higashiyama et al., *Science* 251:936–939, 1991). A common structural feature of these polypeptides is the presence of six cysteine residues that form three disulfide cross links that support a conserved structure that binds to the EGF receptor.

Another member of the EGF family is TGFα and it also binds to the EGF receptor (Todaro et al., *Proc. Natl. Acad. Sci. USA* 77:5258–5262, 1980). TGFα stimulates the EGF receptor's tyrosine kinase activity and has many cellular functions, such as stimulating a mitogenic response in a wide variety of cell types. TGFα and EGF mRNAs reach their highest levels and relative abundance (compared to total RNA in the early postnatal period and decrease thereafter, suggesting a role in embryonic development. From a histological perspective, TGFα acts on numerous cell types throughout the body. The active form of TGFα is derived from a larger precursor and contains 50 amino acids. TGFα shares only a 30% structural similarity with the 53-amino acid form of EGF, but including conservation of all six cysteine residues. TGFα is highly conserved among species. For example, the rat and human polypeptides share about 90% homology as compared to a 70% homology as between the rat and human EGF polypeptide. The amino acid sequence of human TGFα is shown in SEQ ID NO. 1. The sequence shows that a family consisting of vaccinia growth factor, amphiregulin precursor, betacellulin precursor, heparin binding EGF-like growth factor, epiregulin (rodent only), HUS 19878 and schwannoma derived growth factor have similar sequence motifs and can be considered as members of the same family based upon their shared cysteine disulfide bond structures.

TGFα is an acid and heat stable polypeptide of about 5.6 kDa molecular weight. It is synthesized as a larger 30–35 kDa molecular weight glycosylated and membrane-bound precursor protein wherein the soluble 5.6 kDa active form is released following specific cleavage by an elastase-like protease. TGFα binds with high affinity in the nanomolar range and induces autophosphorylation to transduce signal with the EGF receptor. TGFα is 50 amino acids in length and has three disulfide bonds to forms its tertiary configuration. All three disulfide bonds must be present for activity. TGFα is stored in precursor form in alpha granules of secretory cells. Moreover, the primary amino acid sequence is highly conserved among various species examined, such as more than 92% homology at the amino acid level as between human and rat TGFα polypeptides.

TGFα has been investigated extensively and has recently been identified as useful for treating a patient with a neurological deficit. This mechanism is thought to stimulate proliferation and migration of neural-origin stem cells to those sites or lesions in a deficit. For example, Parkinson's Disease is characterized by resting tremor, rigidity, inability to initiate movement (akinesia) and slowness of movement (bradykinesia). The motor deficits are associated with progressive degeneration of the dopaminergic innervation to the nucleus accumbens and degeneration of noradrenergic cells of the locus ceruleus and serotonergic neurons of the raphe. Up to 80% of nigral dopamine neurons can be lost before significant motor deficits are manifest. TGFα (full polypeptide) was shown, when infused into rat brains, was useful for the treatment of neurodegenerative disorders. Intracerebroventricular (ICV) or intrastriatal infusions of TGFα induced neuronal stem cell proliferation, but degenerating or damaged or otherwise abnormal cells needed to be present to facilitate migration of the neuronal stem cells to a site of injury on a scale sufficient to impact recovery from an associated neurological deficit. Forebrain neural stem cells, that give rise to migrating progenitor cells that affect treatment and recovery from a neurological deficit disorder, are the migrating cells that affect treatment recovery from a neural deficit disorder (e.g., Parkinson's Disease, Huntington's Disease, Alzheimer's Disease and the like).

Neural stem cells have been found in subependyma throughout the adult rodent CNS (Ray et al. *Soc. Neurosci.* 22:394.5, 1996) and in the subependyma of adult human forebrain (Kirschenbaum et al., *Cerebral Cortex* 4:576–589, 1994). Thus, the discovery that TGFα stimulates proliferation of neural stem cells and promotes migration to a site of injury or deficit has led to its investigation for the treatment of a neurodegenerative disorder (Alzheimer's Disease, Huntington's Disease and Parkinson's Disease) or CNS traumatic injury (e.g., spinal chord injury), demyelinating disease, CNS inflammatory disease, CNS autoimmune disease (e.g., multiple sclerosis) or CNS ischemic disease (e.g., stroke or brain attack).

A CNS stem cell has the potential to differentiate into neurons, astrocytes and to exhibit replication of itself to provide a resource for self-renewal. Both neurons and glial cells seem to be derived from a common fetal precursor cell. In the vertebrate CNS, multipotential cells have been identified in vitro and in vivo. Certain mitogens, such as TGFα, can cause proliferation of CNS mutipotential cells in vitro and this is the basis for a procedure to harvest such cell, treat them ex vivo to stimulate proliferation in culture and then readminister such cells. Immunohistochemical analysis in the human brain supports the notion that TGFα is widely distributed in neurons and glial cells both during development and during adulthood. In mice genetically altered to lack expression of functioning TGFα, there was a decrease in neural progenitor cell proliferation in forebrain subependyma, providing evidence for TGFα as a proliferative factor for neural progenitor cells.

TGFα is found mainly in various neurons of the CNS during development and in the adult brain in the cerebral neocortex, hippocampus and striatum. It is also found in glial cells, primarily in the cerebral and cerebellar cortex areas. Northern blot analyses showed that TGFα and not EGF (epidermal growth factor) is the most abundant ligand that binds to the EGF receptor in the brain. TGFα mRNA levels were 15–170 times higher than EGF in cerebellum and cerebral cortex. TGFα also appears in germinal centers of the brain during neurogenesis and gliogenesis in the developing brain. In the midbrain, the distribution of TGFα overlaps with tyrosine hydroxylase mRNA and fetal dopaminergic neurons. In culture, TGFα enhanced survival and neurite outgrowth of neonatal rat dorsal ganglion neurons (EGF did not) and survival and differentiation of CNS neurons. TGFα induced proliferation of neural precursor cells of the murine embryonic mesencephalon and further induced a significant increase in the number of astroglia and microglia in fetal rat medial septal cells. TGFα increased glutamic acid decarboxylase activity and decreased choline actetyltransferase activity. Thus, TGFα acted as a general neuronal survival factor affecting both cholinergic and GABAergic neurons. In addition, TGFα is a mitogen for pluripotent brain stem cells. Forebrain subependyma contains nestin positive neural stem cells and their progeny, which are constitutively proliferating progenitor epithelial cells. A "knockout" mouse that was genetically engineered to delete the gene for TGFα showed a reduction in neuronal progenitor cells in the subependyma and a reduction in neuronal progenitors that migrate to the olifactory bulb. In vitro, TGFα promoted dopamine uptake in fetal rat dopaminergic neurons in a dose-dependent and time-dependent manner. TGFα selectively promoted dopaminergic cell survival, enhanced neurite length, branch number and the soma area of tyrosine hydroxylase immunopositive cells. The levels of TGFα were elevated in ventricular cerebrospinal fluid in juvenile parkinsonism and Parkinson's Disease and may represent a compensatory response to neurodegeneration. Further, TGFα prevented a striatal neuronal degeneration in an animal model of Huntington's Disease.

The mucosal epithelium of the intestine is in a continually dynamic state known as "epithelial renewal" in which undifferentiated stem cells from a proliferative crypt zone divide, differentiate and migrate to the luminal surface. Once terminally differentiated, they are sloughed from the tips of the villi. The turnover of the crypt-villus cell population is rapid and occurs every 24–72 hours. Continuous exfoliation of the cells at the villus tip is counterbalanced by ongoing proliferation in the crypt so that net intestinal epithelial mass remains relatively constant. The rapidly-proliferating epithelium of the gastrointestinal tract is extremely sensitive to cytotoxic drugs that are widely used in the chemotherapy of cancer. This "side effect" reduces the tolerated dose of such drugs as it can cause a breakdown of the GI barrier function and septic condition in a patient already immunocompromised. This can also lead to life-threatening hemorrhage. Therefore, there is a need in the art for the development of products and delivery systems that stimulate the repair and rejuvenation of mucosal epithelium in the gastrointestinal tract to provide benefit to patient receiving chemotherapy and radiation therapy for cancer.

Therefore, there is a need in the art to find improved TGFα mimetic agents that are more economical to produce and are smaller (in terms of molecular weight). The present invention was made to address such a need.

SUMMARY OF THE INVENTION

The present invention is based upon two basic discoveries that have not been reported before in the literature of TGFα. Firstly, a novel genus of small peptides, much smaller than (50 amino acid human) TGFα, was discovered as having TGFα biological activity and therefore are useful as pharmacologic (therapeutic) agents for the same indications as full-length TGFα polypeptide (50 or 57 amino acids). Secondly, TGFα and the genus of smaller peptide fragments disclosed herein, were found to have therapeutic activity to stimulate hematopoiesis in patients undergoing cytotoxic cancer chemotherapy and to act as a cytoprotective agent to protect a patient undergoing cancer cytotoxic therapy from gastrointestinal (GI) side effects, such as mucositis and otherwise support the barrier function of the GI tract when it is harmed by cytotoxic therapy.

The present invention provides a compound that acts as a TGF-α mimetic, comprising at least an 11-membered peptide compound from formula I:

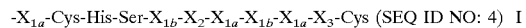
-$X_{1a}$-Cys-His-Ser-$X_{1b}$-$X_2$-$X_{1a}$-$X_{1b}$-$X_{1a}$-$X_3$-Cys (SEQ ID NO: 4)    I wherein $X_{1a}$ and $X_{1b}$ are independently Val, Gly or Ala wherein $X_2$ is Tyr or Phe, wherein $X_3$ is Arg or Lys, and wherein the two Cys moieties form a disulfide bond to create an 11-amino acid loop peptide. Preferably at least one or more of the following seven amino acids, are added to the C terminus Cys residue from formula II:

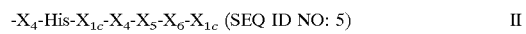
-$X_4$-His-$X_{1c}$-$X_4$-$X_5$-$X_6$-$X_{1c}$ (SEQ ID NO: 5)    II wherein $X_4$ is Glu or Asp, wherein $X_5$ is Leu or Ile, and wherein $X_6$ is Asp, Glu or Leu. Preferably, $X_{1a}$ is Val, $X_{1b}$ is Gly in formula I, and $X_{1c}$ is Ala in formula II. Preferably $X_2$ is Tyr and $X_3$ is Arg. Most preferably, the loop peptide is 13 amino acids in length wherein $X_{1a}$ is Val, $X_{1b}$ is Gly, $X_{1c}$ is Ala and $X_4$ is Glu.

The present invention finer provides a pharmaceutical composition comprising a loop peptide in a pharmaceutically acceptable carrier, wherein the loop peptide compound comprises at least an 11-membered peptide compound from formula I:

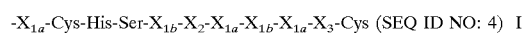
-$X_{1a}$-Cys-His-Ser-$X_{1b}$-$X_2$-$X_{1a}$-$X_{1b}$-$X_{1a}$-$X_3$-Cys (SEQ ID NO: 4)    I wherein $X_{1a}$ and $X_{1b}$ are independently Val, Gly or Ala wherein $X_2$ is Tyr or Phe, wherein $X_3$ is Arg or Lys, and wherein the two Cys moieties form a disulfide bond to create an 11-amino acid loop peptide. Preferably at least one or more of the following seven amino acids, are added to the C terminus Cys residue from formula II:

-$X_4$-His-$X_{1c}$-$X_4$-$X_5$-$X_6$-$X_{1c}$ (SEQ ID NO: 5)    II wherein $X_4$ is Glu or Asp, wherein $X_5$ is Leu or Ile, and wherein $X_6$ is Asp, Glu or Leu. Preferably, $X_{1a}$ is Val, $X_{1b}$ is Gly in formula I, and $X_{1c}$ is Ala in formula II. Preferably $X_2$ is Tyr and $X_3$ is Arg. Most preferably, the loop peptide is 13 amino acids in length wherein $X_{1a}$ is Val, $X_{1b}$ is Gly, $X_{1c}$ is Ala and $X_4$ is Glu.

The present invention further provides a method for treating a neurodegenerative disease with a pharmaceutically active loop peptide or a pharmaceutically active TGFα57 polypeptide, wherein the loop peptide comprises at least an 11-membered peptide compound from formula I or a polypeptide from formula III, wherein formula I is:

$X_{1a}$-Cys-His-Ser-$X_{1b}$-$X_2$-$X_{1c}$-$X_{1b}$-$X_{1a}$-$X_3$-Cys (SEQ ID NO: 4)   I wherein $X_{1a}$ and $X_{1b}$ are independently Val, Gly or Ala wherein $X_2$ is Tyr or Phe, wherein $X_3$ is Arg or Lys, and wherein the two Cys moieties form a disulfide bond to create an 11-amino acid loop peptide; wherein formula III is:

Loop peptide-N-terminus-linker-cyclic $C_4H_8N_2$-linker-Loop peptide-N-terminus   II wherein the linker moiety is designed to link the N-terminus of the Loop peptide to a nitrogen atom of the ring $C_4H_8N_2$ and wherein the "loop peptide" comprises at least an 11-membered peptide compound from formula I; wherein $X_{1a}$ and $X_{1b}$ are independently Val, Gly or Ala wherein $X_2$ is Tyr or Phe, wherein $X_3$ is Arg or Lys, and wherein the two Cys moieties form a disulfide bond to create an 11-amino acid loop peptide; and wherein TGFα57 is a 57 amino acid polypeptide having the formula IV:

Ser-Leu-Ser-Leu-Pro-Ala-Met-N-Human TGFα-COOH (SEQ ID NO: 3)   IV wherein human TGFα is a 50 amino acid polypeptide having the formula of SEQ ID NO: 1. Preferably at least one or more of the following seven amino acids, are added to the C terminus Cys residue from formula II:

-$X_4$-His-$X_{1c}$-$X_4$-$X_5$-$X_6$-$X_{1c}$ (SEQ ID NO: 5)   II wherein $X_4$ is Glu or Asp, wherein $X_5$ is Leu or Ile, and wherein $X_6$ is Asp, Glu or Leu. Preferably, $X_{1a}$ is Val, $X_{1b}$ is Gly in formula I, and $X_{1c}$ is Ala in formula II. Preferably $X_2$ is Tyr and $X_3$ is Arg. Most preferably, the loop peptide is 13 amino acids in length wherein $X_{1a}$ is Val, $X_{1b}$ is Gly, $X_{1c}$ is Ala and $X_4$ is Glu.

The present invention further provides a method for enhancing hermatopoiesis during cytotoxic or immune-suppressing therapy, comprising administering a TGFα polypeptide or a TGFα57 polypeptide or a pharmaceutically active loop peptide or a combination thereof, wherein the loop peptide comprises at least an 11-membered peptide compound from formula I:

-$X_{1a}$-Cys-His-Ser-$X_{1b}$-$X_2$-$X_{1a}$-$X_{1b}$-$X_{1c}$-$X_3$-Cys (SEQ ID NO: 4)   I wherein $X_{1a}$ and $X_{1b}$ are independently Val, Gly or Ala wherein $X_2$ is Tyr or Phe, wherein $X_3$ is Arg or Lys, and wherein the two Cys moieties form a disulfide bond to create an 11-amino acid loop peptide; and wherein TGFα57 is a 57 amino acid peptide having the formula IV:

Ser-Leu-Ser-Leu-Pro-Ala-Met-N-Human TGF α-COOH (SEQ ID NO: 3)   IV wherein human TGFα is a 50 amino acid polypeptide having the formula of SEQ ID NO: 1. Preferably at least one or more of the following seven amino acids, are added to the C terminus Cys residue from formula II:

-$X_4$-His-$X_{1c}$-$X_4$-$X_5$-$X_6$-$X_{1c}$ (SEQ ID NO: 5)   II wherein $X_4$ is Glu or Asp, wherein $X_5$ is Leu or Ile, and wherein $X_6$ is Asp, Glu or Leu. Preferably, $X_{1a}$ is Val, $X_{1b}$ is Gly in formula I, and $X_{1c}$ is Ala in formula II. Preferably $X_2$ is Tyr and $X_3$ is Arg. Most preferably, the loop peptide is 13 amino acids in length wherein $X_{1a}$ is Val, $X_{1b}$ is Gly, $X_{1c}$ is Ala and $X_4$ is Glu.

Preferably the invention further comprises administering a second hematopoietic growth factor agent to stimulate more mature hematopoietic precursor cells, wherein the second hematopoietic growth factor is selected from the group consisting of erythropoietin, thrombopoietin, G-CSF (granulocyte colony stimulating factor), and GM-CSF (granulocyte macrophage colony stimulating factor). Preferably, the invention further comprises administering stem cell factor (SCF) to augment CD34 positive progenitor cells.

The present invention further provides a method for treating or preventing mucositis of the gastrointestinal tract caused by cytotoxic or immune-suppressing therapy, comprising administering a TGFα polypeptide or a TGFα57 polypeptide or a pharmaceutically active loop peptide or a combination thereof, wherein the loop peptide comprises at least an 11-membered peptide compound from formula I:

-$X_{1a}$-Cys-His-Ser-$X_{1b}$-$X_2$-$X_{1a}$-$X_{1b}$-$X_{1c}$-$X_3$-Cys (SEQ ID NO: 4)   I wherein $X_{1a}$ and $X_{1b}$ are independently Val, Gly or Ala wherein $X_2$ is Tyr or Phe, wherein $X_3$ is Arg or Lys, and wherein the two Cys moieties form a disulfide bond to create an 11-amino acid loop peptide; and wherein TGFα57 is a 57 amino acid peptide having the formula IV:

Ser-Leu-Ser-Leu-Pro-Ala-Met-N-Human TGFα-COOH (SEQ ID NO: 3)   IV wherein human TGFα is a 50 amino acid polypeptide having the formula of SEQ ID NO: 1. Preferably at least one or more of the following seven amino acids, are added to the C terminus Cys residue from formula II:

-$X_4$-His-$X_{1c}$-$X_4$-$X_5$-$X_6$-$X_{1c}$ (SEQ ID NO: 5)   II wherein $X_4$ is Glu or Asp, wherein $X_5$ is Leu or Ile, and wherein $X_6$ is Asp, Glu or Leu. Preferably, $X_{1a}$ is Val, $X_{1b}$ is Gly in formula I, and $X_{1c}$ is Ala in formula II. Preferably $X_2$ is Tyr and $X_3$ is Arg. Most preferably, the loop peptide is 13 amino acids in length wherein $X_{1a}$ is Val, $X_{1b}$ is Gly, $X_{1c}$ is Ala and $X_4$ is Glu.

The present invention further provides a bifunctional compound that acts as a TGFα mimetic, comprising a compound from formula III:

Loop peptide-N-terminus-linker-cyclic $C_4H_8N_2$-linker-Loop peptide-N-terminus   III wherein the linker moiety is desired to link the N-terminus of the Loop peptide to a nitrogen atom of the ring $C_4H_8N_2$ and wherein the "loop peptide" comprises at least an 11-membered peptide compound from formula I:

-$X_{1a}$-Cys-His-Ser-$X_{1b}$-$X_2$-$X_{1a}$-$X_{1b}$-$X_{1c}$-$X_3$-Cys (SEQ ID NO: 4)   I wherein $X_{1a}$ and $X_{1b}$ are independently Val, Gly or Ala wherein $X_2$ is Tyr or Phe, wherein $X_3$ is Arg or Lays, and wherein the two Cys moieties form a disulfide bond to create an 11-amino acid loop peptide; and wherein TGPα57 is a 57 amino acid polypeptide having the formula IV:

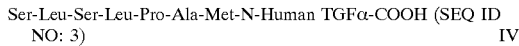
Ser-Leu-Ser-Leu-Pro-Ala-Met-N-Human TGFα-COOH (SEQ ID NO: 3)    IV wherein human TGPα is a 50 amino acid polypeptide having the formula of SEQ ID NO: 1. Preferably at least one or more of the following seven amino acids, are added to the C terminus Cys residue from formula II:

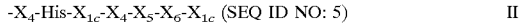
-$X_4$-His-$X_{1c}$-$X_4$-$X_5$-$X_6$-$X_{1c}$ (SEQ ID NO: 5)    II wherein $X_4$ is Glu or Asp, wherein $X_5$ is Leu or Ile, and wherein $X_6$ is Asp, Glu or Leu. Preferably, $X_{1a}$ is Val, $X_{1b}$ is Gly in formula I, and $X_{1c}$ is Ala in formula II. Preferably $X_2$ is Tyr and $X_3$ is Arg. Most preferably, the loop peptide is 13 amino acids in length wherein $X_{1a}$ is Val, $X_{1b}$ is Gly, $X_{1c}$ is Ala and $X_4$ is Glu.

The present invention further provides a method for treating inflammatory bowel disease, colitis, and Chron's Disease of the gastrointestinal tract, comprising administering a TGFα polypeptide or a TGFα57 polypeptide or a pharmaceutically active loop peptide or a combination thereof, wherein the loop peptide comprises at least an 11-membered peptide compound from formula I:

-$X_{1a}$-Cys-His-Ser-$X_{1b}$-$X_2$-$X_{1a}$-$X_{1b}$-$X_{1a}$-$X_3$-Cys (SEQ D NO: 4)    I wherein $X_{1a}$ and $X_{1b}$ are independently Val, Gly or Ala wherein $X_2$ is Tyr or Phe, wherein $X_3$ is Arg or Lys, and wherein the two Cys moieties form a disulfide bond to create an 11-amino acid loop peptide;
and wherein TGFα57 is a 57 amino acid peptide having the formula IV:

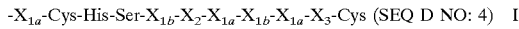
Ser-Leu-Ser-Leu-Pro-Ala-Met-N-Human TGFα-COOH (SEQ ID NO: 3)    IV wherein human TGFα is a 50 amino acid polypeptide having the formula of SEQ ID NO: 1. Preferably at least one or more of the following seven amino acids, are added to the C terminus Cys residue from formula II:

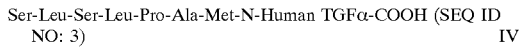
-$X_4$-His-$X_{1c}$-$X_4$-$X_5$-$X_6$-$X_{1c}$ (SEQ ID NO: 5)    II wherein $X_4$ is Glu or Asp, wherein $X_5$ is Leu or Ile, and wherein $X_6$ is Asp, Glu or Leu. Preferably, $X_{1a}$ is Val, $X_{1b}$ is Gly in formula I, and $X_{1c}$ is Ala in formula II. Preferably $X_2$ is Tyr and $X_3$ is Arg. Most preferably, the loop peptide is 13 amino acids in length wherein $X_{1a}$ is Val, $X_{1b}$ is Gly, $X_{1c}$ is Ala and $X_4$ is Glu.

The present invention further provides a method for treating an inflammatory reaction of autoimmune diseases, comprising administering a TGFα polypeptide or a TGFα57 polypeptide or a pharmaceutically active loop peptide or a combination thereof, wherein the loop peptide comprises at least an 11-membered peptide compound from formula I:

-$X_{1a}$-Cys-His-Ser-$X_{1b}$-$X_2$-$X_{1a}$-$X_{1b}$-$X_{1a}$-$X_3$-Cys (SEQ ID NO: 4)    I wherein $X_{1a}$ and $X_{1b}$ are independently Val, Gly or Ala wherein $X_2$ is Tyr or Phe, wherein $X_3$ is Arg or Lys, and wherein the two Cys moieties form a disulfide bond to create an 11-amino acid loop peptide;
and wherein TGFα57 is a 57 amino acid peptide having the formula IV:

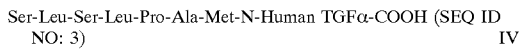
Ser-Leu-Ser-Leu-Pro-Ala-Met-N-Human TGFα-COOH (SEQ ID NO: 3)    IV wherein human TGFα is a 50 amino acid polypeptide having the formula of SEQ ID NO; 1. Preferably the autoimmune diseases are selected from the group consisting of Type II (Juvenile) Diabetes, rheumatoid arthritis, lupus and multiple sclerosis. Preferably, at least one or more of the following seven amino acids, are added to the C terminus Cys residue from formula II:

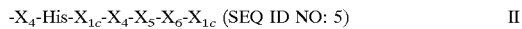
-$X_4$-His-$X_{1c}$-$X_4$-$X_5$-$X_6$-$X_{1c}$ (SEQ ID NO: 5)    II wherein $X_4$ is Glu or Asp, wherein $X_5$ is Leu or Ile, and wherein $X_6$ is Asp, Glu or Leu. Preferably, $X_{1a}$ is Val, $X_{1b}$ is Gly in formula I, and $X_{1c}$ is Ala in formula II. Preferably $X_2$ is Tyr and $X_3$ is Arg. Most preferably, the loop peptide is 13 amino acids in length wherein $X_{1a}$ is Val, $X_{1b}$ is Gly, $X_{1c}$ is Ala and $X_4$ is Glu.

Figure 8:
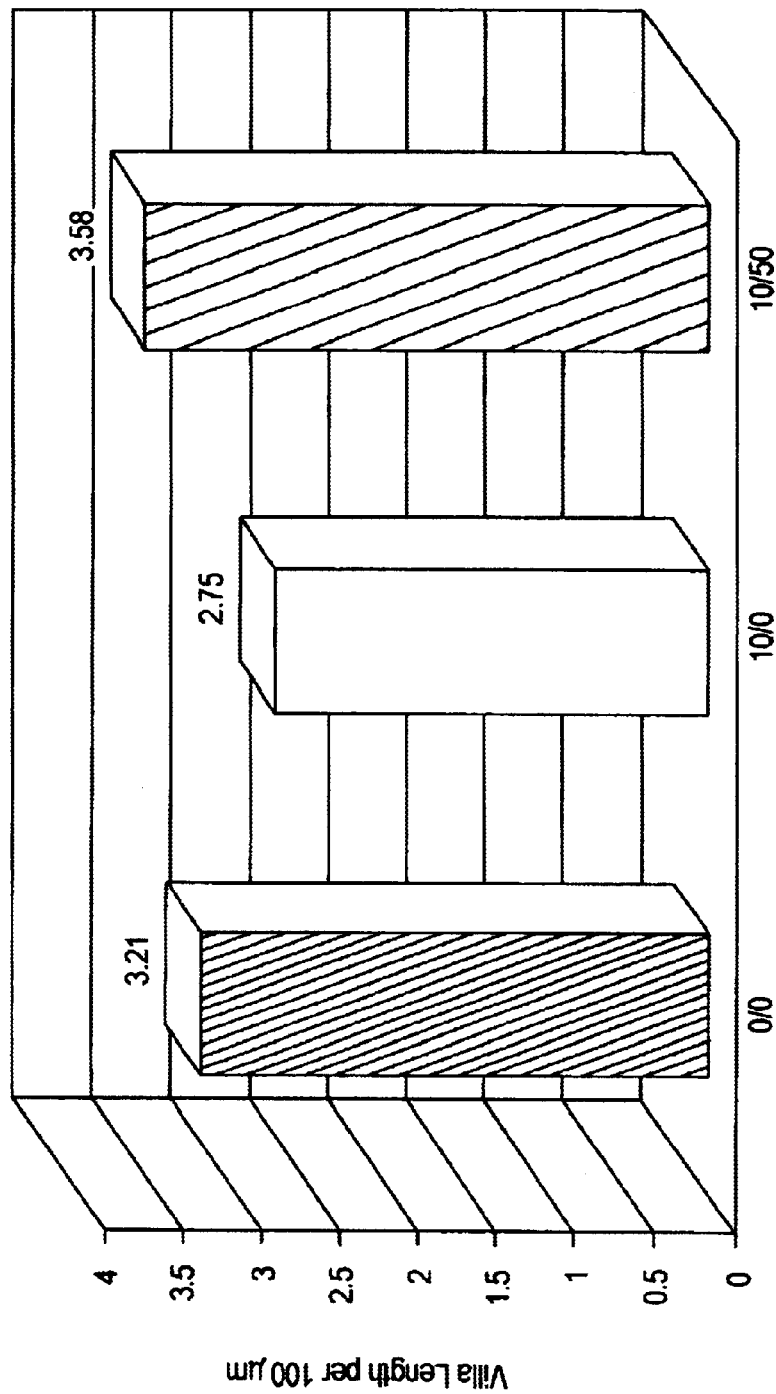

The histological data is summarized in FIG. 8 that measured average crypt height of the three groups of mice. TGFα57 treatment (50 ng/g) was able to more-than-restore crypt height loss from CP treatment.

FIGS. 9A–9C show the three panels at 160× magnification to correspond to a normal duodenum intestine section in the top panel, CP only treated (10 µg/g) in the middle panel and both CP (10 µg/g) and TGFα57 (50 ng/g) in the bottom panel. In the normal intestine (top panel), each villus extends from the luminal surface to the basal muscularis mucosal surface. Goblet cells are scattered and predominate in the base of the villus (arrows) whereas columnar absorptive cells line the luminal surface. In the middle panel, the alcian blue staining method shows that the villi contain a fewer number of goblet cells (than normal) (arrows). The injured absorptive and goblet cells are degenerating at the tip of the villi (arrows). Abundant secretory mucus material is stained in the luminal surface (arrows). In the bottom panel, there was an increased number of goblet cells scattered throughout the villi (arrows). The intestinal villi are in normal form with elongation. The majority of enterocytes are not alcian blue stained positive. The luminal plasma membranes of the villi (arrows) are well protected by TGFα treatment.

Figure 10:
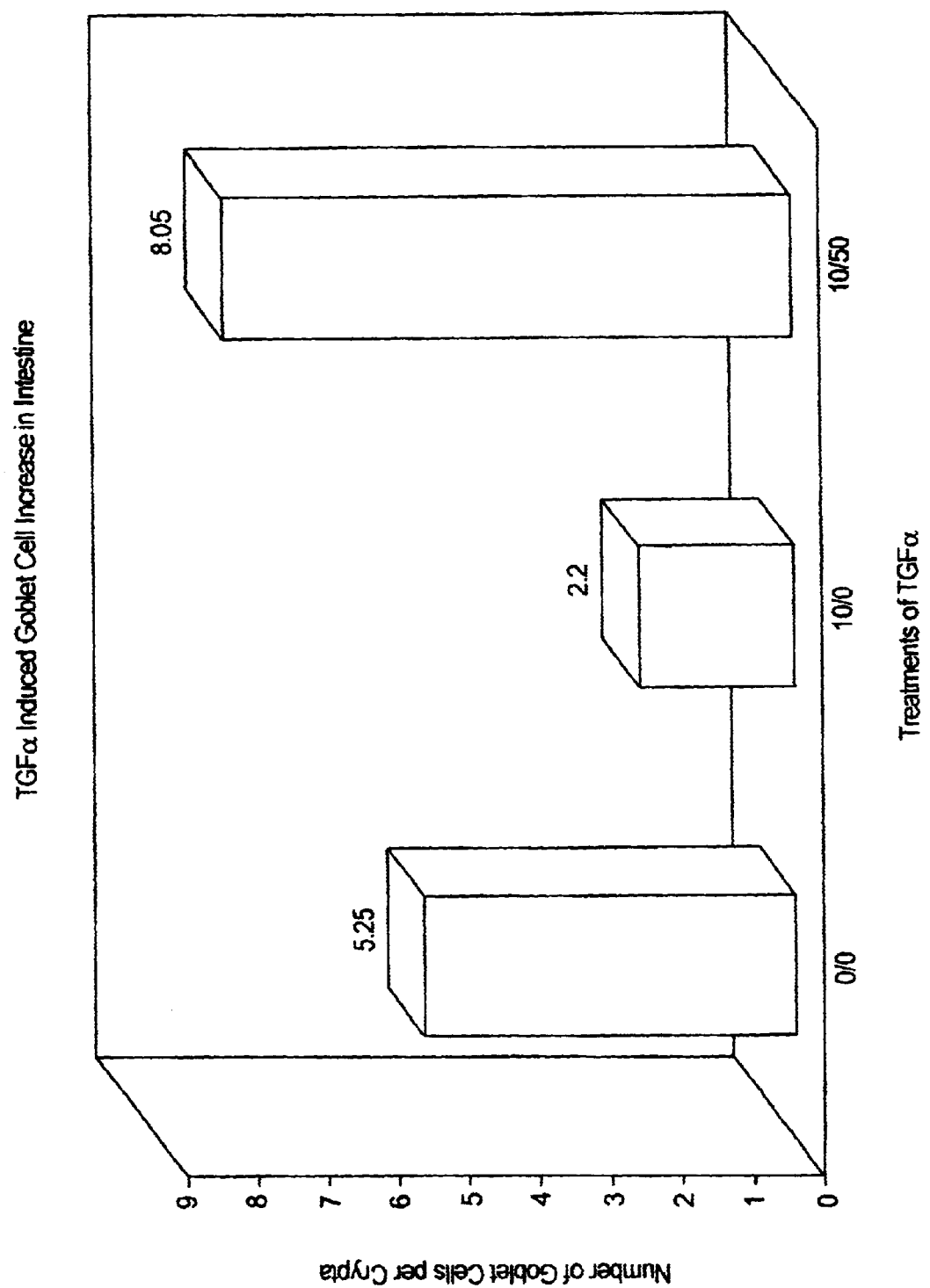

FIG. 10 shows that TGFα57 treatment not only increased the number of goblet cells but also increased the number from CP treatment to a higher level than normal intestine.

FIGS. 11A and 11B show that TGFα57 treatment causes mast cells residing in the intestinal mucosal tissue and lamina propria to remain intact and thus not release hista-mine and other pro-inflammatory molecules. The bottom panel, by contrast, shows CP-treated mice who did not receive TGFα57 wherein there was a degranulation of mast cells and subsequent induction of inflammatory responses.

DETAILED DESCRIPTION OF THE INVENTION

Loop Peptide

Figure 1:
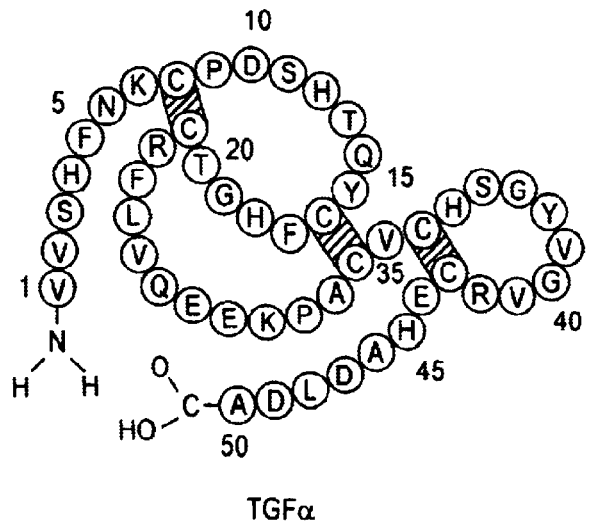
FIG. 1 shows the structure of rat TGFα polypeptide and its 50 amino acids arranged into three loops. The human TGFα sequence is provided in SEQ ID NO. 1 with a similar tertiary structure and a close sequence homology.
Figure 2:
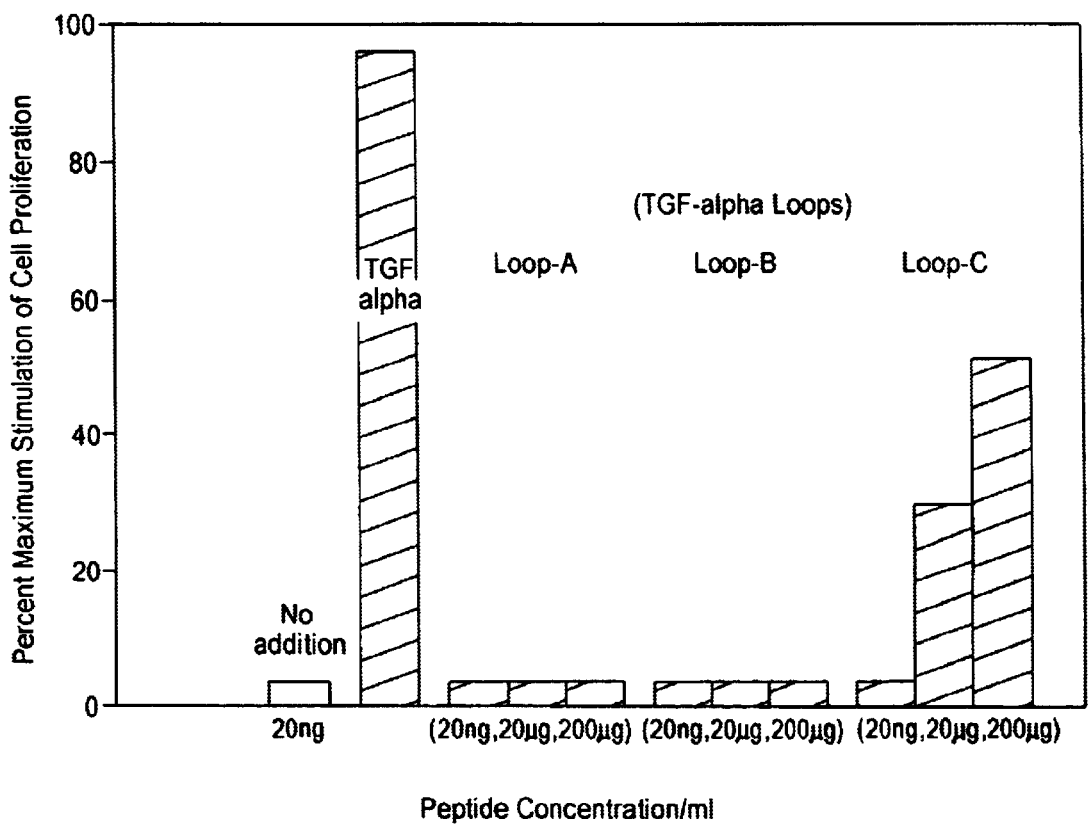
FIG. 2 shows a graph comparing TGFα biological activity of the three loop peptide regions of TGFα (see FIG. 1) wherein Loop A is amino acids 1–21 (starting at the N terminus), Loop B is amino acids 16 to 32 and Loop C is amino acids 33 to 50. Only Loop C showed significant TGFα activity as determined by cell proliferation and in a dose response fashion.

Human TGFα is a polypeptide of 50 amino acids and the corresponding rat sequence is shown in FIG. 1. The human or rat TGFα polypeptide can be divided roughly into three loop regions corresponding roughly (starting at the N terminus) to amino acids 1–21, to amino acids 16–32, and to amino acids 33–50. Each of the three foregoing loop regions in human TGFα was investigated for TGFα-like biological activity, such as stimulation of cellular proliferation as measured by $^3$H thymidine incorporation of stem cells. As shown in FIG. 2, only the Loop C peptide (corresponding to amino acids 33–50) showed significant TGFα biological activity and is therefore a TGFα mimetic peptide. Therefore, in view of the fact that the loop peptide exhibited TGFα biological activity, data obtained with TGFα (50 amino acid polypeptide or even the altered splice 57 amino acid polypeptide) is predictive. Accordingly, data from TGFα or TGFα57 show what can be called "TGFα activity" and these area are predictive of activity of the loop peptide and similar loop peptides embodied in the genus of formula I with or without the addition of a "tail" region of formula II. These data predict activity for the loop peptide when activity is also shown for TGFα or for TGFα57.

Pharmaceutical Composition and Formulations

The inventive pharmaceutical composition comprises a loop peptide in a pharmaceutically acceptable carrier. The pharmaceutically acceptable carrier is suitable for the particular form of administration contemplated by the pharmaceutical composition. The term "carrier" is designed to mean any and all solvents, dispersion media, coatings, isotonic agents, antibacterial and antifungal agents designed to preserve a formulation from contamination, absorption agents and similar agents that are compatible with pharmaceutical administration irrespective of the route of administration.

The pharmaceutical formulations are made based upon the intended routes of administration. Specifically, those formulations that will be intended for a GI indication may be administered orally. In view of the peptide bonds present, such formulations will be made to pass through the stomach and protect the active compound from the low pH conditions of the stomach before there is a better chance for local activity in the villi of the small intestine and large intestine. The loop peptide formulations are intended for parenteral administration through some form of injection or for use in ex vivo culture media. Parenteral forms of administration include, for example, intravenous, intradermal, intramuscular, intraperitoneal for GI effects, injection directly into a target organ (e.g., brain) at the appropriate location, application in a biodegradable matrix to a site of CNS injury (e.g., spinal cord).

Solutions or suspensions useful in the pharmaceutical compositions that contain peptide components include sterile diluents such as water, saline, fixed oils, polyethylene glycols, glycerine, propylene glycol, or other synthetic agents, plus an antibacterial or antifungal agent for preservation, antioxidants, chelating agents, buffer and agents that adjust tonicity for direct organ injections. Forms of pharmaceutical compositions include, for example, sterile aqueous solutions or dispersions and sterile powders for the extemporaneous preparation of sterile injectable solutions of dispersions. For intravenous injection or direct organ or peritoneal injections, suitable carriers include, for example, saline, bacteriostatic water, Cremophor, or phosphate buffered saline. The composition is formulated to preserve stability, be easily mixed and preserved against contamination. Isotonic agents, such as sugars or polyalcohols (e.g., glucose, fructose, mannitol, sorbitol and the like) or sodium chloride are used. Agents that delay target organ absorption can also be used and these include, for example, aluminum monostearate and gelatin.

Sterile injectable solutions can be prepared by incorporating the active agent (see formula I, formula II, or formula III and TGFα) in the required amount in an appropriate solvent and then sterilizing, such as by sterile filtration. Further, powders can be prepared by standard techniques such as freeze drying or vacuum drying.

In another embodiment, the active agent is prepared with a biodegradable carrier for sustained release characteristics for either sustained release in the GI tract or for target organ implantation (e.g., brain or spinal cord) with long term active agent release characteristics to the intended site of activity (such as a site of injury or neuronal degradation). Biodegradable polymers include, for example, ethylene vinyl acetate, polyanhydrides, polyglycolic acids, polylactic acids, collagen, polyorthoesters, and poly acetic acid. Liposomal formulation can also be used.

In addition, the active compound for the pharmaceutical composition needs to also be synthesized. If the compound is from formula I or formula II, a preferred means for synthesizing peptides of 13–18 amino acids in length is by direct peptide synthesis generally starting with the N-terminal amino acid and adding amino acids in the C terminal direction. Such small peptides can also be synthesized and later purified by standard recombinant techniques, but peptide of 18 amino acids in length are better synthesized from the amino acid building blocks directly. TGFα has bee made using recombinant techniques and is available as a laboratory reagent commercially. The bifunctional compounds of formula III are best synthesized with each loop peptide moiety synthesized and then added to the heterocyclic nitrogen atom using standard heterocyclic addition synthesis Loop Peptide Mimics TGFα Neuroactive Therapeutic Activity The neuroactive activity of the loop peptide is based upon the discovery that the loop peptide exhibits TGFα biological activity and can therefore stimulate CNS multipotent precursor cells to divide and migrate through the brain. This activity indicates that the loop peptide is effective to treat neurological deficits caused by a wide variety of diseases and injuries that each result in a neurological deficit in some specific area of the brain or specific kind of neuron. These include degenerative diseases, including the more common Alzheimer's Disease (AD), Parkinson's Disease (PD), and Huntington's Disease (HD), and the less common Pick's disease, progressive supranuclear palsy, striatonigral degeneration, cortico-basal degeneration, olivopontocerebellar atrophy, Leigh's disease, infantile necrotizing encephalomyelopathy, Hunter's disease, mucopolysaccharidosis, various leukodystrophies (such as Krabbe's disease, Pelizaeus-Merzbacher disease and the like), amaurotic (familial) idiocy, Kuf's disease, Spielmayer-Vogt disease, Tay Sachs disease, Batten disease, Jansky-Bielschowsky disease, Reye's disease, cerebral ataxia, chronic alcoholism, beriberi, Hallervorden-Spatz syndrome, cerebellar degeneration, and the like.

Further, injuries (traumatic or neurotoxic) that cause a loss of neuronal function can be treated by the loop peptide. Such injuries include, for example, gunshot wounds, injuries caused by blunt force, penetration injuries, injuries caused by surgical procedure (e.g., tumor removal, abscess removal, epilepsy lesion removal) poisoning (e.g., carbon monoxide), shaken baby syndrome, adverse reactions to medications, drug overdoses, and post-traumatic encephalopathy. Ischemia can further cause CNS injury due to disruption of blood flow or oxygen delivery that can kill or injure neurons and glial cells. Such injuries can be treated by administration of the loop peptide and include, for example, injuries caused by stroke, anoxia, hypoxia, partial drowning, myoclonus, severe smoke inhalation, dystonias, and acquired hydrocephalus. Developmental disorders that can be treated by the loop peptide include, for example, schizophrenia, certain forms of severe mental retardation, cerebral palsey, congenital hydrocephalus, severe autism, Downs Syndrome, LHRH/hypothalamic disorder, and spina bifida. The loop peptide can be further used to treat disorders affecting vision caused by the loss or failure of retinal cells and include, for example, diabetic retinopathy, serious retinal detachment (associated with glaucoma), traumatic injury to the retina, retinal vascular occlusion, macular degeneration, optic nerve atrophy and other retinal degenerative diseases. Injuries to the spinal cord can be treated by the loop peptide. Examples of spinal cord injuries are post-polio syndrome, amyotrophic lateral sclerosis, traumatic injury, surgical injury, and paralytic diseases. Demylinating autoimmune disorders can be treated by administration of the loop peptide and include, for example, multiple sclerosis. Lastly, the loop peptide can be used to treat neurological deficits caused by infection of inflammatory diseases, including, for example, Creutzfeldt-Jacob disease and other slow virus infectious diseases of the CNS, AIDS encephalopathy, post-encephalitic Parkinsonism, viral encephalitis, bacterial meningitis and other CNS effects of infectious diseases.

The loop peptide provides TGFα activity and therefor the present method of treating neurological deficit and injury disorders is based upon the biological activity of the loop peptide of formula I, formula II and formula III and the data available for TGFα that has been published.

Hematopoiesis

Figure 3:
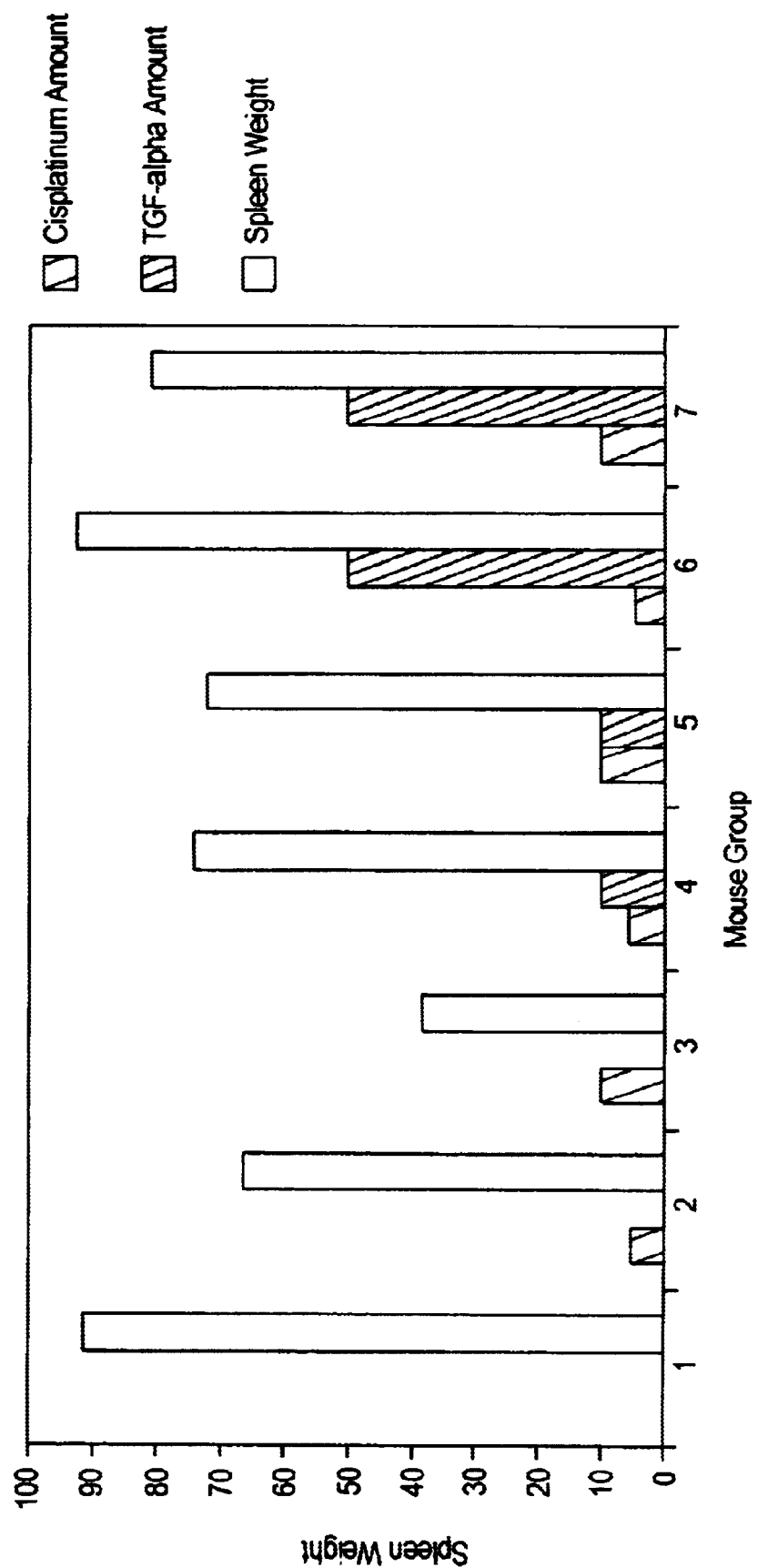
FIG. 3 shows a graph of mouse spleen weights that were treated with Cis Platinum (CP) at either 5 $\mu$g/g or 10 $\mu$g/g and with TGFα at concentrations of 10 ng/g or 50 ng/g. These data show that TGFα treatment caused a return to normal spleen weights despite CP treatment that reduced spleen weights significantly.

TGFα and related polypeptides, such as TGFα57, showed surprising enhancing activity in an in vivo model of general hematopoiesis when administered in conjunction with a potent cytotoxic agent Cis Platinum (CP). FIG. 3 shows a graph of mouse spleen weights that were treated with CP at either 5 μ/g or 10 μg/g and with TGFα57 at concentrations of 10 ng/g or 50 ng/g. These data show that TGFα57 treatment caused a return to normal spleen weights despite CP treatment that reduced spleen weights significantly. This in vivo experiment is a predictive model for hematopoiesis in humans as CP is a cytotoxic agent commonly used for cancer chemotherapy that is known to significantly reduce trilineage hematopoietic cells. Hematopoietic cells are red blood cell precursors, platelet precursors (megakaryocytes), and immune (white) blood cell precursors of various forms of T cells, B cells and macrophages. Moreover, platelet counts were higher in those mice injected with TGFα57 (and CP) as opposed to CP alone where such counts were significantly reduced from normal. It should be noted that references to TGFα as a human 50 amino acid polypeptide further include reference to human TGFα57 as an alternative cleavage variant.

The experiment procedure dosed those animals to be treated with TGFα57 4 hours prior to challenge with CP. A single dose of CP was administered. Additional doses (as indicated) of TGFα57 were made at 24 hours, 48 hours, 72 hours and 96 hours after the CP dose. All doses were made by IP injection. Controls were dosed with saline instead of either or both of CP and TGFα57.

The animals were sacrificed about 4 hours after the last TGFα57 (or saline) dose. Key organs were removed and spleens were immediately weighed after a clean incision. All the relevant organs were placed in formalin, transported for histopathological analysis, mounted, sectioned, stained and observed. The results of this histological analysis of the spleens for hematopoietic effect and the GI tract (below) provide the surprising data of the effect of TGFα57 activity.

Figure 4:
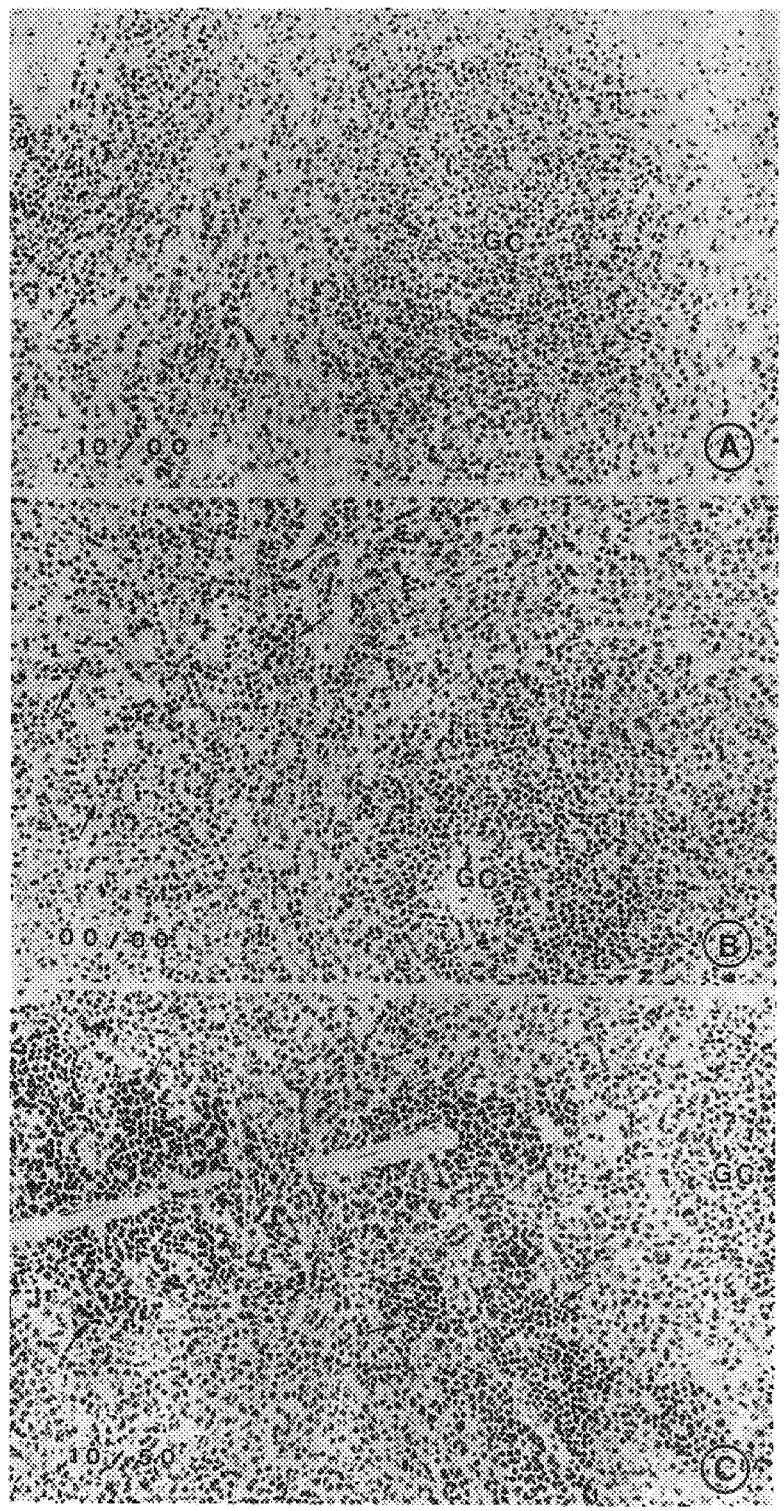
FIGS. 4a–4c, show three panels of H&E-stained spleens. Specifically, the top panel spleens show a CP-treated mouse spleen (10 $\mu$g/g) showing apoptotic cells (densely stained with fragments of nuclei) in the germinal center (GC). The T cells within the central arterial area show the absence of a marginal zone and much fewer erythrocytes and T cells in the perifolecular area (arrows). In the middle panel, a normal mouse spleen is shown (no CP and no TGFα) fixed in formalin showing an arteriole with T cells areas (arrow). A primary follicle and a second follicle are shown as containing a germinal center (GC). There is a presence of an erythrocyte rich (pink) perifollicular zone surrounding both a T cell and B cell compartments of white pulp. In the bottom panel, a mouse spleen treated with CP (10 $\mu$g/g) and TGFα57 (50 ng/g) shows an increased number of T cells and erythrocytes in the perifolicular zone (arrows). The T cell area contains lymph vessels in relation to arterioles. A germinal center (GC) is within the mantle zone.

In FIG. 4, three panels of H&E-stained spleens are shown. Specifically, the top panel shows a CP-treated mouse spleen (10 μg/g) showing apoptotic cells (densely stained with fragments of nuclei) in the germinal center (GC). The T cells with the central arterial area show the absence of a marginal zone and much fewer erythrocytes and T cells in the perifolecular area (arrows). In the middle panel, a normal mouse spleen is shown (no CO and no TGFα57) fixed in formalin showing an arteriole with T cells areas (arrow). A primary follicle and a second follicle are shown as containing a germinal center (GC). There is a presence of an erythrocyte rich (pink) perifollicular zone surrounding both a T cell and B cell compartments of white pulp. In the bottom panel, a mouse spleen treated with CP (10 μg/g) and TGFα57 (50 ng/g) shows an increased number of T cells and erythrocytes in the perifolicular zone (arrows). The T cell area contains lymph vessels in relation to arterioles. A germinal center (GC) is within the mantle zone. These in vivo data in a predictive model of hematopoiesis and confirmed by blinded histological analysis (the histologist/pathologist was blinded as to the treatment history of the coded tissues received) providing surprising evidence of the utility of peptides having TGFα activity to augment hematopoiesis following cytotoxic exposure. These data predict and provide a reasonable correlation that TGFα and the peptides of formula I, formula II and formula III are useful therapeutic agents for enhancing hematopoiesis following or during cytotoxic therapy, such as cancer treatment. Therefore, a useful method for treating cancer is to combine either TGFα or a peptide from formula I, formula II, formula III, of formula IV or combinations thereof with cytotoxic treatment regimens to reduce dose-limiting side effects of cytotoxic agents.

An additional experiment investigated TGFα activity (using TGFα57) FACS-sorted human CD34 positive and CD38 negative cells were cultured in liquid primary cultures in Iscove's modified Dulbecco's media with supplements. TGFα (57) was added alone (10 ng/ml) and exhibited a 35% increase in CD34 positive progenitor cells. Stem Cell Factor (SCF) was used as a positive control (500 ng/ml) and provided a three-fold increase in CD34 positive cells. When a combination of SCF (500 ng/ml) and TGFα (10 ng/ml) was added, a synergistic 12-fold increase in CD34 positive cells was observed.

Moreover, the present invention provides a combination therapeutic agent for augmenting hematopoiesis in patients treated for cancer, comprising a TGFα polypeptide or mimetic thereof in combination with SCF. The effect of TGFα or mimetics thereof is to augment hematopoiesis and increase the bone marrow population of CD34+cells. SCF also can augment bone marrow populations of CD34[+] cells but also has a side effect of mast cell degranulation that is dose limiting. Therefore, the ability of TGFα and mimetics thereof to both augment hematopoiesis and alleviate the dose limiting side effect of SCF provides for a synergistic combination therapeutic agent.

Mucositis and Gastrointestinal Diseases

The small intestine comprises the duodenum, jejunum and ileum. It is the principal site for absorption of digestive products from the GI tract. Digestion begins in the stomach and is completed in the small intestine in association with the absorptive process. The intestinal mucosa surface is made up of numerous finger-like projections called villi. In addition, mucosa between the basis of the villi (crypts) is formed into the crypts.

Figure 5:
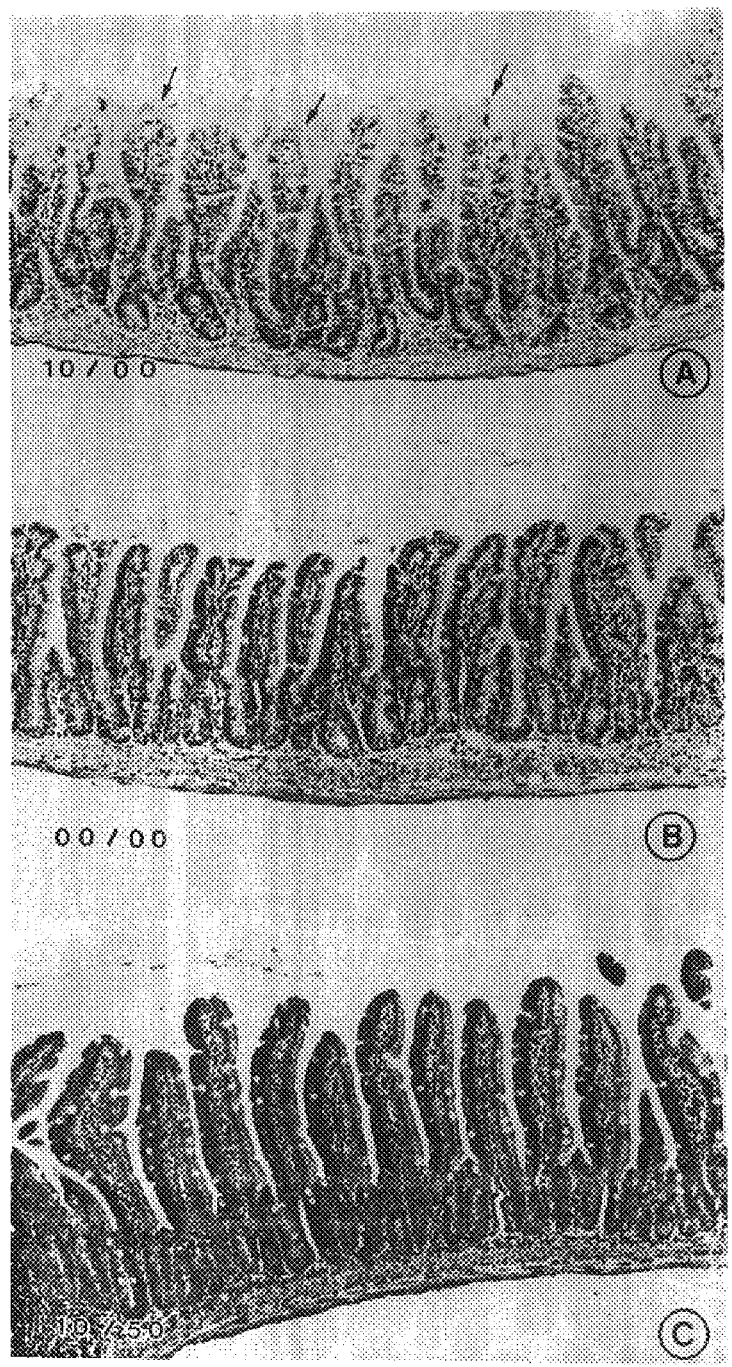
FIGS. 5A–5C show the histological examination of mouse intestines. In the top panel, CP (single intraperitoneal (ip) dose 10 $\mu$g/g) treated intestine is cross-sectioned at the duodenum and shows significant injury to the villi. Specifically, the villi are necrotic and the crypts are in irregular shapes. The tips of the crypts were losing their cellular integrity (arrows). In the middle panel is a cross section of a normal mouse GI tract (no CP and no TGFα57) and shows a normal duodenum intestinal surface with villi having long and slender mucosal projections with a core of lamina propria covered by a luminal epithelial layer. A single row of intestinal crypt is found at the base of mucosa. These crypts that lie between adjacent villi are surrounded by the same lamina propria that form the villous cores. Both columnar absorptive cells and goblet cells cover the villous surfaces. The goblet cells contain apical clear vacuoles. The bottom panel shows a cross section of a mouse duodenum intestine exposed with both the CP (10 µg/g) and TGFα57 (50 ng/g). The intestinal structure is very similar to the normal intestinal structure. Specifically, the villus is long and slender. Both absorptive cells and goblet cells are visible at the surface of the villi. There is an abundant amount of goblet cells on the surface.

TGFαor a peptide from formula I, formula II, formula III, or formula IV having TGFα activity or combinations thereof are also useful for treating mucositis associated with intestinal bleeding, dyspepsia caused by with cytotoxic therapy and for improving the barrier function of the GI tract compromised by cytotoxic therapy. The in vivo experiment with seven groups of mice described above for hematopoietic effects noted in spleens also examined the GI tract of these treated mice. In FIG. 5 there are three panels showing the histological examination of mouse intestines. In the top panel, CP (single ip dose of 10 μg/g) treated intestine is cross-sectioned and shows significant injury to the villi. Specifically, the villi are necrotic and the crypts are in irregular shapes. The tips of the crypts were losing their cellular integrity (arrows). In the middle panel is a cross section of a normal mouse GI tract (no CP and no TGFα57) and shows a normal intestinal surface with villi having long and slender mucosal projections with a core of lamina propria covered by a luminal epithelial layer. A single row of intestinal crypt is found at the base of the mucosa. These crypts that lie between adjacent villi are surrounded by the same lamina propria that form the villous cores. Both columnar absorptive cells and goblet cells cover the villous surfaces. The goblet cells contain apical clear vacuoles. The bottom panel shows a cross section of a mouse intestine exposed to both the CP (10 μg/g) and TGFα57 (50 ng/g). The intestinal structure is very similar to the normal intestinal structure. Specifically, the villus is long and slender. Both absorptive cells and goblet cells are visible at the surface of the villi. There is an abundant amount of goblet cells on the surface.

Figure 6:
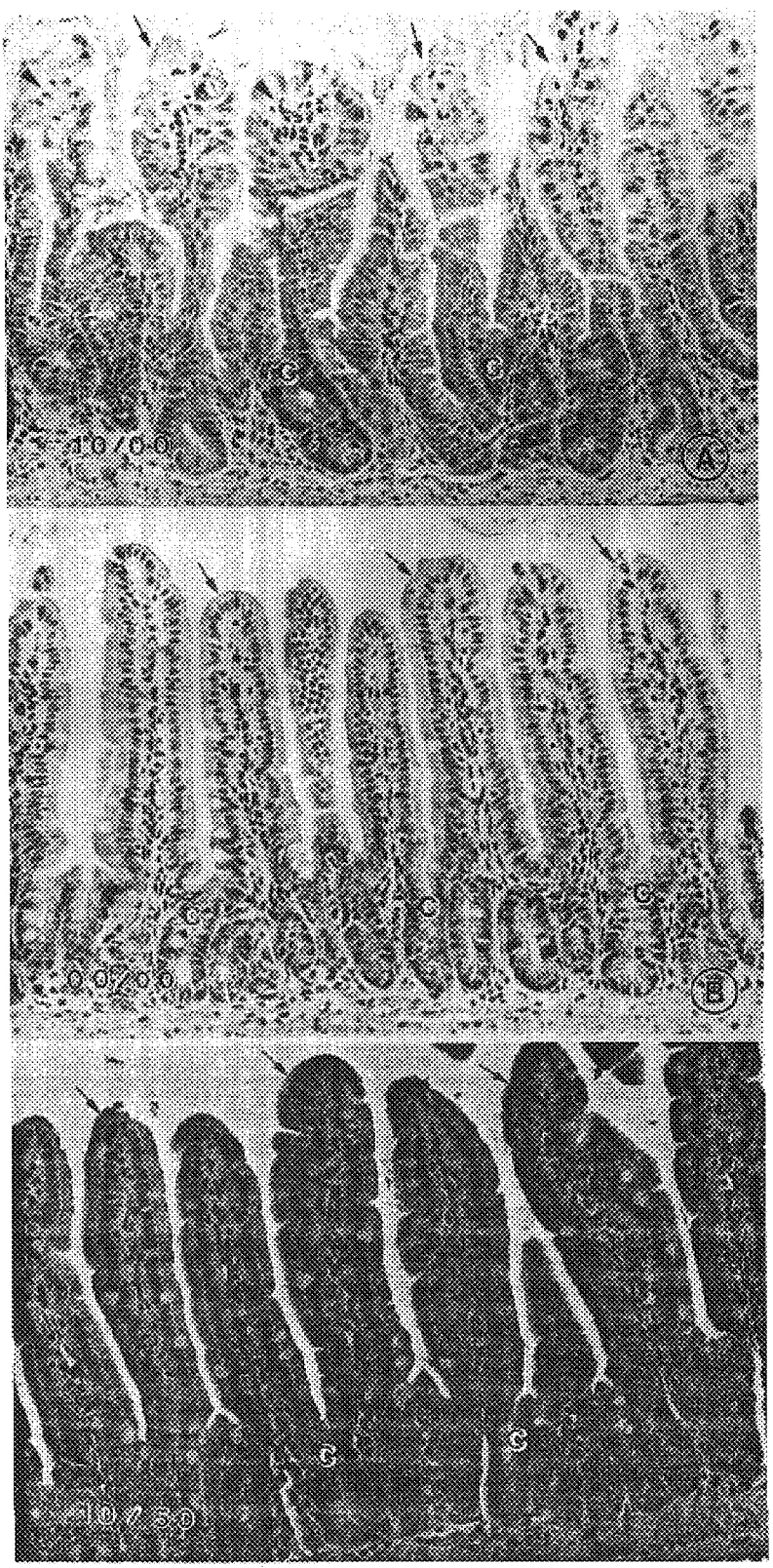
FIGS. 6A–6C show three panels at 160× magnification again corresponding to a CP-treated mouse in the top panel, a normal mouse in the middle panel and a CP treated and TGFα treated mouse in the bottom panel at the same doses as indicated for FIG. 5. In the top panel are injured villi with tips degenerating and necrotic (arrows). Red blood cells are observed in the damaged villi (arrows). The crypts (C) are in irregular shape and in various heights. The middle panel shows that the tips of the villi (arrows) are smooth and the nuclei of the enterocytes are observed throughout the villus. The crypts (C) are similar in height and regular in shape. The bottom panel has villi (arrows) appearing normal as in the middle panel. The crypts (C) also appear to be normal.

In FIG. 6, there are three panels shown at 160× magnification again corresponding to a CP-treated mouse in the top panel, a normal mouse in the middle panel and a CP treated and TGFα57 treated mouse in the bottom panel at the same doses as indicated for FIG. 5. In the top panel are injured villi with tips degenerating and necrotic (arrows). Red blood cells are observed in the damaged villi (arrows). The crypts (C) are in irregular shape and in various heights. The middle panel shows that the tips of the villi (arrows) are smooth and the nuclei of the enterocytes are observed throughout the villus. The crypts (C) are similar in height and regular in shape. The bottom panel has villi (arrows) appearing normal as in the middle panel. The crypts (C) also appear to be normal.

Figure 7:
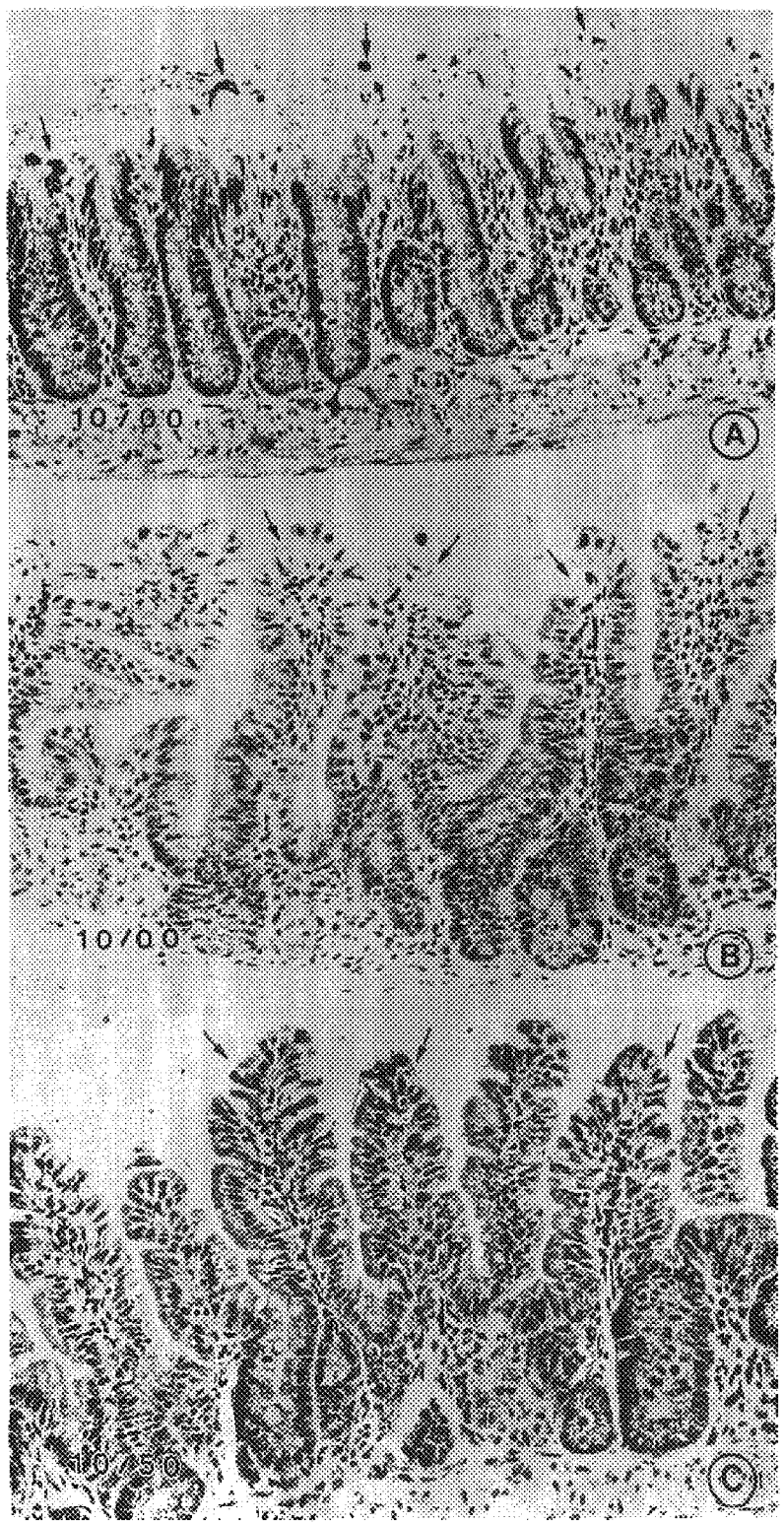
FIGS. 7A–7C show three panels but the top and middle panels are CP (10 µg/g) treated without TGFα and the bottom panel is CP (10 µg/g) and 50 ng/g of TGFα57. The panels are shown at higher magnification. In the top panel, the severely injured crypt surface from CP treatment shows cellular destruction due to necrosis. Red cells appear at the damaged surface to indicate intestinal bleeding. In addition, the middle panel of a CP-treated mouse shows a loss of brush border and very little of a glycocalyx or fuzzy coat. The interspersed globlet cells appear fewer in number (than normal) and are seen as necrotic. In the bottom panel, the effect of TGFα57 treatment shows protection of the villa surface (arrows). Specifically, the epithelial cells are normal appearing with extended brush borders. The nuclei are very densely stained and elongated.

FIG. 7 shows three panels but the top and middle panels are CP (10 μg/g) treated without TGFα57 and the bottom panel is CP (10 μg/g) and 50 ng/g of TGFα57. The panels are shown at higher magnification. In the top panel, the severely injured crypt surface from CP treatment shows cellular destruction due to necrosis. Red cells appear at the damaged surface to indicate intestinal bleeding. In addition, the middle panel of a CP-treated mouse shows a loss of brush border and very little of a glycocalyx or fuzzy coat. The interspersed globlet cells appear fewer in number (than normal) and are seen as necrotic. In the bottom panel, the effect of TGFα treatment shows protection of the villa surface (arrows). Specifically, the epithelial cells are normal appearing with extended brush borders. The nuclei are very densely stained and elongated. The histological data is summarized in FIG. 8 that measured average crypt height of the three groups of mice. TGFα57 treatment (50 ng/g) was able to more-than-restore crypt height loss from CP treatment.

Figure 9:
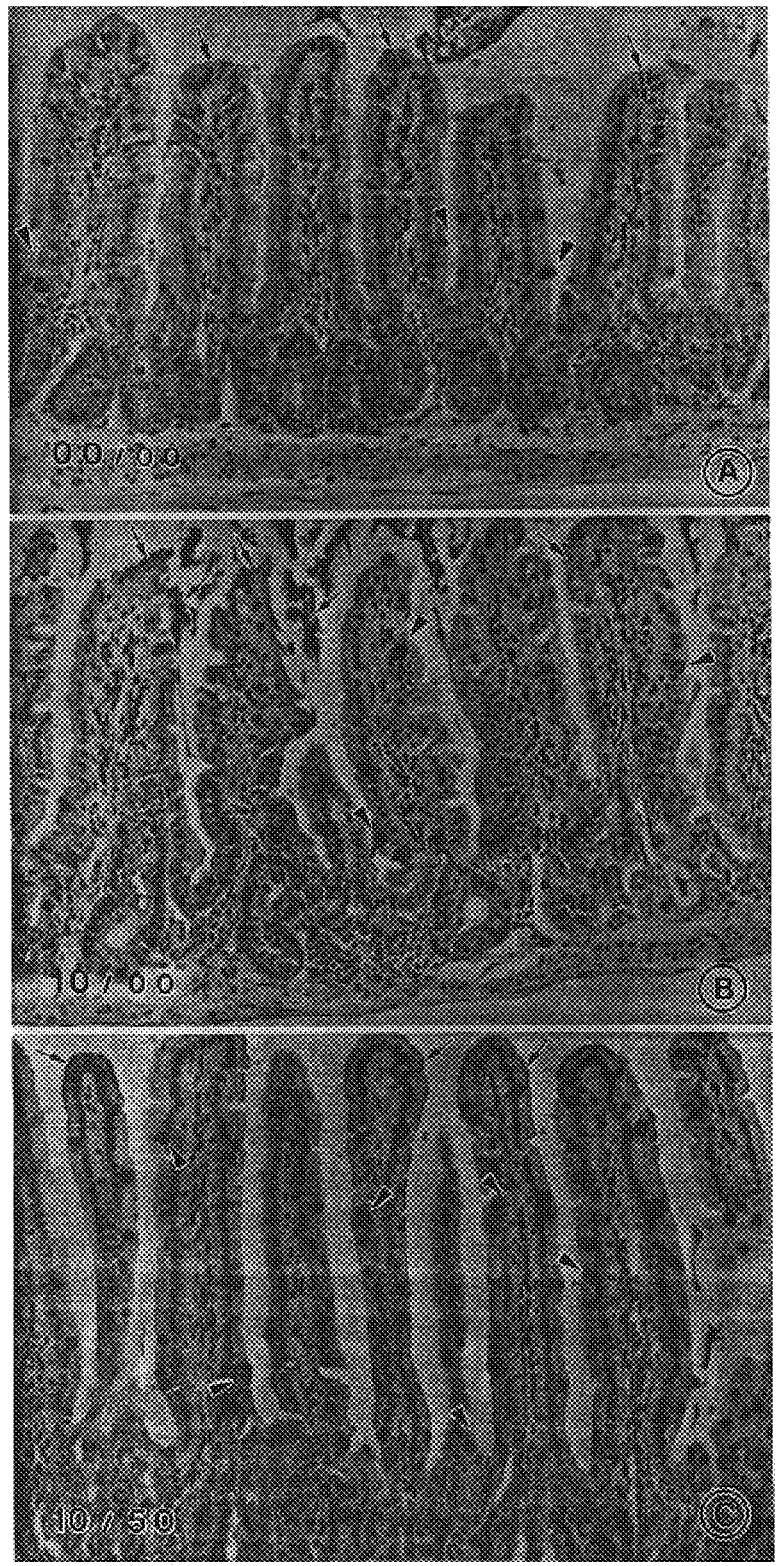

An alcian blue staining method permits differentiation of two major cell types that are an absorptive cell and a goblet cell. The goblet cell mucus is stained a greenish blue color while the absorptive cells remain less stained. In FIG. 9, the three panels at 160× magnification are shown to correspond to normal intestine in the top panel, CP only treated (10 μg/g) in the middle panel and both CP (10 μg/g) and TGFα57 (50 ng/g) in the bottom panel. In the normal intestine (top panel), each villus extends from the luminal surface to the basal muscularis mucosal surface. Goblet cells are scattered and predominate in the base of the villus (arrows) whereas columnar absorptive cells line the luminal surface. In the middle panel, the alcian blue staining method shows that the villi contain a fewer number of goblet cells (than normal) (arrows). The injured absorptive and goblet cells are degenerating at the tip of the villi (arrows). Abundant secretory mucus material is stained in the luminal surface (arrows). In the bottom panel, there are an increased number of goblet cells scattered throughout the villi (arrows). The intestinal villi are in normal form with elongation. The majority of enterocytes do not appear to be alcian blue stained positive. The luminal plasma membranes of the villi (arrows) are well protected by TGFα treatment. The number of goblet cells was counted on the average unit length of intestine. These data are shown in FIG. 10. TGFα treatment not only increased the number of goblet cells but also increased the number from CP treatment to a higher level than normal intestine.

Accordingly, these data show the effects of TGFα, and the loop peptides from formula I, formula II, formula III, and formula IV having therapeutic activity to treat or prevent mucositis associated with cytotoxic therapy and for inflammatory bowel diseases. Moreover, the histological effect showing that there was a prevention of mast cell degranulation (FIG. 11), provides additional data supporting the gastrointestinal applications for TGFα, and the loop peptide of formula I, formula II, formula III, and formula IV.

Autoimmune Diseases

In addition, TGFα activity resulted in stimulation of proliferation of select immune cells (particularly of the T cell lineage) after administration to mice after immune-suppression of CP administration. The stimulated immune cells were phenotypically identified as CD4 positive T cells and double null CD4 negative CD8 negative T cell progenitors with characteristics of NK-1 cells. Thus, TGFα activity (specifically from TGFα57 administration) resulted in regulated immune functions and in particular defects in NK-1 cells. Therefore, these data predict that TGFα activity and the loop peptide of formula I, formula II, formula III, and formula IV will be effective in treating autoimmune diseases by mitigating over-inflammatory reactions. The in vivo activity of TGFα (FIG. 11) (and the loop peptide of formula I, formula II, formula III, and formula IV) to stimulate early T cell progenitors on the NK-1 type results in the release of TH-2 cytokines and this down regulates autoimmune phenomena. The stimulation of select immune cells, in particular cells of a T cell lineage, was seen consistently in the mice who received CP and TGFα57 (FIG. 11 for GI tract) in lymphoid tissue, Peyers Patches and the spleen. Further, recruitment of help via CD4 cells in some cases boosts immune system function in general.

Figure 11:
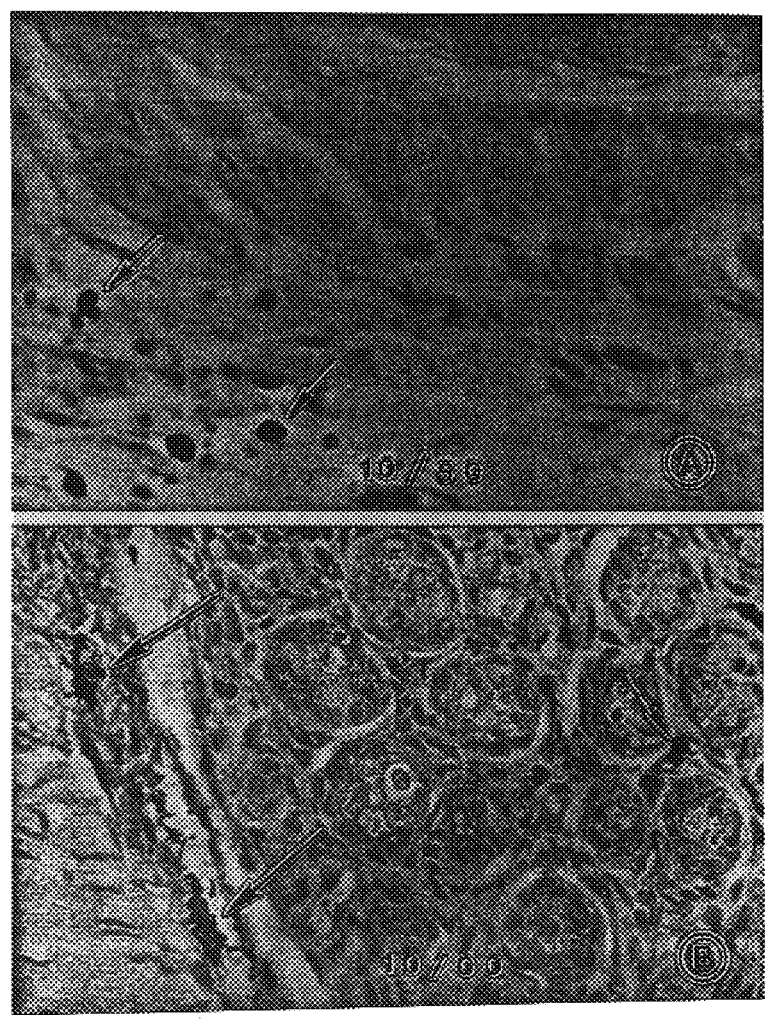

In FIG. 11, TGFα administration prevented mast cell degranulation and subsequent histamine release. This is a parallel activity that is in addition to the gastrointestinal anti-inflammatory activity and prevention of mucositis of TGFα (and the loop peptide of formula I, formula II, formula III, and formula IV) described herein.

We claim:

1. A method for treating or preventing mucositis of the gastrointestinal tract from cytotoxic of immune-suppressing therapy, comprising administering TGFα (SEQ ID NO: 1) or TGFα57 (SEQ ID NO: 3).

2. The method of claim 1, wherein the peptide is administered intraperitoneally.

3. A method for treating or preventing mucositis of the gastrointestinal tract from cytotoxic or immune-suppressing therapy, comprising administration of a pharmaceutically active loop peptide comprising amino acids 33–50 of SEQ ID NO: 1.

4. A method for treating or preventing mucositis of the gastrointestinal tract from cytotoxic or immune-suppressing therapy, comprising administration of a TGFα polypeptide and an 11-amino acid loop peptide of formula I:

$$-X_{1a}\text{-Cys-His-Ser-}X_{1b}\text{-}X_2\text{-}X_{1a}\text{-}X_{1b}\text{-}X_{1a}\text{-}X_3\text{-Cys-} \quad \text{I}$$

wherein $X_{1a}$ is Val, $X_{1b}$ is Gly, $X_2$ is Tyr, and $X_3$ is Arg, and wherein the two Cys residues form a disulfide bond to create an 11-amino acid loop peptide.

5. A method for treating or preventing mucositis of the gastrointestinal tract from cytotoxic or immune-suppressing therapy, comprising administration of TGFα57 and an 11-amino acid loop peptide of formula I:

$$-X_{1a}\text{-Cys-His-Ser-}X_{1b}\text{-}X_2\text{-}X_{1a}\text{-}X_{1b}\text{-}X_{1a}\text{-}X_3\text{-Cys-} \quad \text{I}$$

wherein $X_{1a}$ is Val, $X_{1b}$ is Gly, $X_2$ is Tyr, and $X_3$ is Arg, and wherein the two Cys residues form a disulfide bond to create an 11-amino acid loop peptide.

* * * * *

SEQUENCE LISTING

<160> NUMBER OF SEQ ID NOS: 5

<210> SEQ ID NO 1
<211> LENGTH: 50
<212> TYPE: PRT
<213> ORGANISM: Homo sapiens

<400> SEQUENCE: 1

Val Val Ser His Phe Asn Asp Cys Pro Asp Ser His Thr Gln Phe Cys
1               5                   10                  15

Phe His Gly Thr Cys Arg Phe Leu Val Gln Glu Asp Lys Pro Ala Cys
            20                  25                  30

Val Cys His Ser Gly Tyr Val Gly Ala Arg Cys Glu His Ala Asp Leu
        35                  40                  45

Leu Ala
    50

<210> SEQ ID NO 2
<211> LENGTH: 50
<212> TYPE: PRT
<213> ORGANISM: Rattus norvegicus

<400> SEQUENCE: 2

-continued

```
Val Val Ser His Phe Asn Lys Cys Pro Asp Ser His Thr Gln Tyr Cys
1               5                   10                  15

Phe His Gly Thr Cys Arg Phe Leu Val Gln Glu Lys Pro Ala Cys
            20                  25                  30

Val Cys His Ser Gly Tyr Val Gly Val Arg Cys Glu His Ala Asp Leu
            35                  40                  45

Asp Ala
    50

<210> SEQ ID NO 3
<211> LENGTH: 57
<212> TYPE: PRT
<213> ORGANISM: Artificial sequence
<220> FEATURE:
<223> OTHER INFORMATION: A modified human TGF-alpha sequence

<400> SEQUENCE: 3

Ser Leu Ser Leu Pro Ala Met Val Val Ser His Phe Asn Asp Cys Pro
1               5                   10                  15

Asp Ser His Thr Gln Phe Cys Phe His Gly Thr Cys Arg Phe Leu Val
            20                  25                  30

Gln Glu Asp Lys Pro Ala Cys Val Cys His Ser Gly Tyr Val Gly Ala
            35                  40                  45

Arg Cys Glu His Ala Asp Leu Leu Ala
    50                  55

<210> SEQ ID NO 4
<211> LENGTH: 11
<212> TYPE: PRT
<213> ORGANISM: Artificial sequence
<220> FEATURE:
<223> OTHER INFORMATION: Artificial peptide sequence
<220> FEATURE:
<221> NAME/KEY: VARIANT
<222> LOCATION: (1)..(10)
<223> OTHER INFORMATION: Xaa at residue 1, 5, 7 to 9 is independently V,
      G or A; Xaa at residue 6 is Y or F; and Xaa at residue 10 is R or
      K

<400> SEQUENCE: 4

Xaa Cys His Ser Xaa Xaa Xaa Xaa Xaa Xaa Cys
1               5                   10

<210> SEQ ID NO 5
<211> LENGTH: 7
<212> TYPE: PRT
<213> ORGANISM: Artificial sequence
<220> FEATURE:
<223> OTHER INFORMATION: Artificial peptide sequence
<220> FEATURE:
<221> NAME/KEY: VARIANT
<222> LOCATION: (1)..(7)
<223> OTHER INFORMATION: Xaa at residue 1 and 4 is E or D; Xaa at
      residue 3 and 7 is V, G, or A; Xaa at residue 5 is L or I; and
      Xaa at residue 6 is D or E

<400> SEQUENCE: 5

Xaa His Xaa Xaa Xaa Xaa Xaa
1               5
```